US008460933B2

(12) United States Patent
Rybicki et al.

(10) Patent No.: US 8,460,933 B2
(45) Date of Patent: Jun. 11, 2013

(54) EXPRESSION SYSTEM INCORPORATING A CAPSID PROMOTER SEQUENCE AS AN ENHANCER

(75) Inventors: Edward Peter Rybicki, Cape Town (ZA); Fiona Lesley Tanzer, Cape Town (ZA)

(73) Assignees: South African Medical Research Council, Cape Town (ZA); University of Cape Town, Cape Town (ZA)

(*) Notice: Subject to any disclaimer, the term of this patent is extended or adjusted under 35 U.S.C. 154(b) by 704 days.

(21) Appl. No.: 12/084,728

(22) PCT Filed: Nov. 8, 2006

(86) PCT No.: PCT/IB2006/003150

§ 371 (c)(1),
(2), (4) Date: Jul. 15, 2008

(87) PCT Pub. No.: WO2007/054788

PCT Pub. Date: May 18, 2007

(65) Prior Publication Data

US 2009/0285852 A1 Nov. 19, 2009

(30) Foreign Application Priority Data

Nov. 8, 2005 (ZA) ................................ 2005/09036

(51) Int. Cl.
*C12N 15/67* (2006.01)
*C12N 15/85* (2006.01)
*C12N 5/16* (2006.01)
*A61K 48/00* (2006.01)

(52) U.S. Cl.
USPC ....... 435/455; 435/91.4; 435/320.1; 435/325; 514/44 R; 536/24.1

(58) Field of Classification Search
None
See application file for complete search history.

(56) References Cited

FOREIGN PATENT DOCUMENTS

| | | | |
|---|---|---|---|
| WO | WO 99/45956 | | 9/1999 |
| WO | WO 99/49079 | | 9/1999 |
| WO | WO 99/60140 | | 11/1999 |
| WO | WO 01/61024 | | 8/2001 |
| WO | WO 03/037919 | * | 5/2003 |

OTHER PUBLICATIONS

Barouch, D. H. et al. Viral escape from dominant simian immunodeficiency virus epitope-specific cytotoxic T lymphocytes in DNA-vaccinated rhesus monkeys. J. Virol. 77, 7367-7375 (2003).*
Desrosier RC "Prospects for an AIDS vaccine" Nature Med. 10(3):221-223; 2004.*
Qiu J-T et al. "Enhancement of Primary and Secondary Cellular Immune Responses against Human Immunodeficiency Virus Type 1 Gag by Using DNA Expression Vectors That Target Gag Antigen to the Secretory Pathway" J. Virology; 74(13):5997-6005.*
Yu et al."Lentiviral Vectors with Two Independent Internal Promoters Transfer High-Level Expression of Multiple Transgenes to Human Hematopoietic Stem-Progenitor Cells" Molecular Therapy, 7(6):827-838; 2003.*
Mankertz et al. "Analysis of transcription of Porcine circovirus type 1" J. Gen Virology; 83:2743-2751; 2002.*
Vandepapeliere P. "Therapeutic vaccination against chronic viral infections" The Lancet Infectious Diseases vol. 2:353-367; 2002.*
Hansen U. et al. "Sequences controlling in vitro transcription of SV40 promoters"The EMBO Journal vol. 2 No. 12 pp. 2293-2303, 1983.*
Stegmeier, F. et al. "A lentiviral microRNA-based system for single-copy polymerase II-regulated RNA interference in mammalian cells" PNAS 102 (37):13212-13217, 2005.*
Mankertz A, Hillenbrand B. Analysis of transcription of Porcine circovirus type 1. J Gen Virol. Nov. 2002;83(Pt 11):2743-51.*
Barouch et al., 2005, "A human T-cell leukemia virus type 1 regulatory element enhances the immunogencity of human immunodeficiency virus type 1 DNA vaccines in mice and nonhuman primates", *Journal of Virology*, 79(14):8828-8834.
Burgers et al., 2006 "Design and preclinical evaluation of a multigene human immunodeficiency virus type 1 subtype C DNA vaccine for clinical trial", *Journal of General Virology*, 87:399-410.
Garmony et al., 2003, "DNA vaccines: improving expression of antigens", *Genet. Vaccines Ther.*, 1:2.
Hatterman et al., 2004, "Infection studies on human cell lines with procine circovirus type 1 and procine circovirus type 2", *Xenotransplantation*, 11:284-294.
Mankertz et al., 2004, "Molecular biology of Porcine circovirus: analyses of gene expression and viral replication", *Veterinary Microbiology*, 98:81-88.

(Continued)

*Primary Examiner* — Mary E Mosher
*Assistant Examiner* — Nick Zou
(74) *Attorney, Agent, or Firm* — Kilpatrick Townsend & Stockton LLP

(57) ABSTRACT

The invention provides a method for enhancing expression of a transgene in a host cell, which includes the steps of inserting a capsid promoter element (Pcap), or a sequence comprising the reverse complement of the capsid promoter element (PcapR), into a mammalian expression cassette upstream (5') of a cytomegalovirus immediate/early enhancer/promoter region (Pcmv); inserting the transgene into the expression cassette downstream (3') of the cytomegalovirus immediate/early enhancer/promoter region; inserting a vector containing the expression cassette into the host organism; and causing expression of the transgene. The capsid promoter element (Pcap) is typically from a circovirus, parvovirus or anellovirus. The transgene is typically expressed at a higher level than when expressed by a vector containing the expression cassette without the transcriptional control element. An expression cassette, vector, DNA vaccine, pharmaceutical composition and method of treatment are also claimed.

10 Claims, 21 Drawing Sheets

OTHER PUBLICATIONS

Quintana et al., 2002, "Experimental inoculation of procine Circoviruses type 1 (PCV1) and type 2 (PCV2) in rabbits and mice", *Vet. Res.*, 33:229-237.

Velten et al., 2005, "Plant viral intergenic DNA sequence repeats with transcription enhancing activity", *Virology Journal*, 2:16.

* cited by examiner

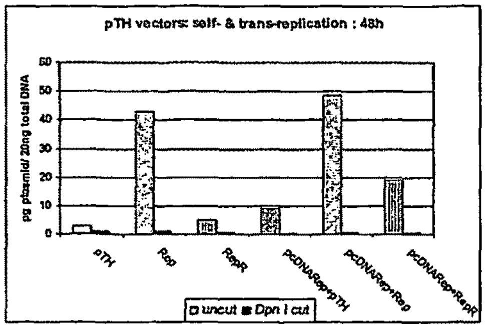
(a)
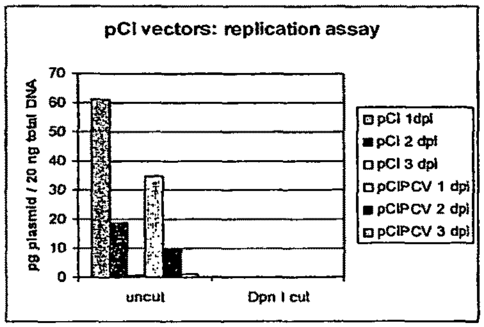
(b)
Fig. 2

- **<u>P*rep*</u> - distinguish replication from promoter effect**

- **replication needs Rep and Rep' proteins encoded by *rep* gene**
- **Both bind to P*rep* - only Rep can inhibit P*rep***

Delete *rep* intron :
– only Rep' is expressed from *rep*
Thus no replication
No repression of P*rep*

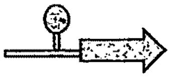

Delete Rep/Rep' binding sites in Prep and all but the 3' terminal portion of *rep*:
No replication
enhanced expression derives from residual Prep

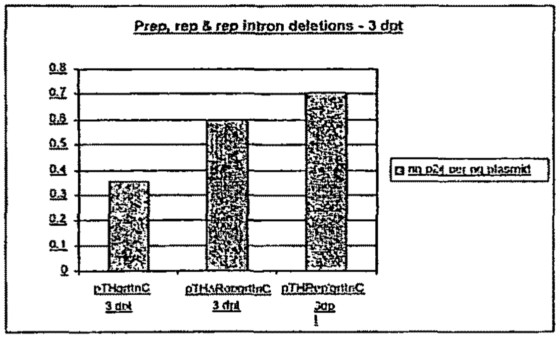

Fig. 3

SEQ Pcap: 190 bp

ORIGIN

```
1      ACTAGTAGGT GTCGCTAGGC TCAGCAAAAT TACGGGCCCA CTGACTCTTC CCACAACCGG
61     GGGGGCCCAC TATGACGTGT ACAGCTGTCT TCCAATCACG CTGCTGCATC TTCCCGCTCA
121    CTTTCAAAAG TTCAGCCAGC CCGCGGAAAT TTCTCACATA CGTTACAGGG AACTGCTCCA
181    TATGACTAGT
```

Fig. 8

SEQ PcapR: 190 bp;

ORIGIN

```
1      ACTAGTCATA TGGAGCAGTT CCCTGTAACG TATGTGAGAA ATTTCCGCGG GCTGGCTGAA
61     CTTTTGAAAG TGAGCGGGAA GATGCAGCAG CGTGATTGGA AGACAGCTGT ACACGTCATA
121    GTGGGCCCGC CCGGTTGTGG GAAGAGTCAG TGGGCCCGTA ATTTTGCTGA GCCTAGCGAC
181    ACCTACTAGT
```

Fig. 9

SEQ grttnC: 3687 bp

ORIGIN

```
1      AAGCTTGCCA CCATGGCTGC TCGCGCATCT ATCCTCAGAG GCGAAAAGTT GGATAAGTGG
61     GAAAAAATCA GACTCAGGCC AGGAGGTAAA AAACACTACA TGCTGAAGCA TATCGTGTGG
121    GCATCTAGGG AGTTGGAGAG ATTTGCACTG AACCCCGGAC TGCTGGAAAC CTCAGAGGGC
181    TGTAAGCAAA TCATGAAACA GCTCCAACCA GCCTTGCAGA CCGGAACAGA AGAGCTGAAG
241    TCCCTTTACA ATACCGTGGC AACCCTCTAT TGCGTCCACG AGAAGATCGA GGTGAGAGAC
301    ACAAAGGAGG CCCTGGACAA AATCGAGGAG GAGCAGAATA AGTGCCAGCA GAAGACCCAG
361    CAGGCAAAGG CTGCTGACGG AAAGGTCTCT CAGAACTATC CTATCGTTCA GAACCTTCAG
421    GGGCAGATGG TGCACCAAGC AATCAGCCCT AGAACCCTGA ACGCATGGGT GAAGGTGATC
481    GAGGAGAAAG CCTTTTCTCC CGAGGTTATC CCCATGTTTA CCGCCCTGAG CGAAGGCGCC
541    ACTCCTCAAG ACCTGAACAC TATGCTGAAC ACAGTGGGAG GACACCAGGC CGCTATGCAG
601    ATGTTGAAGG ATACCATCAA CGAGGAGGCA GCCGAATGGG ACCGCCTCCA CCCCGTGCAC
661    GCCGGACCTA TCGCCCCCGG ACAAATGAGA GAACCTCGCG GAAGTGATAT TGCCGGTACT
721    ACCAGCACCC TTCAAGAGCA GATTGCTTGG ATGACCAGCA ACCCACCCAT CCCAGTGGGC
781    GATATTTACA AAAGGTGGAT TATTCTGGGG CTGAACAAAA TTGTGAGAAT GTACTCCCCC
841    GTCTCCATCC TCGACATCCG CCAAGGACCC AAGGAGCCTT TTAGGGATTA CGTGGACAGA
901    TTCTTCAAAA CCCTTAGAGC TGAGCAAGCC ACTCAGGAGG TTAAGAACTG GATGACAGAT
961    ACTCTGCTCG TGCAAAACGC TAACCCCGAT TGCAAAACCA TCTTGAGAGC TCTCGGTCCA
1021   GGTGCCACCC TTGAGGAAAT GATGACAGCA TGTCAAGGCG TGGGAGGACC TGGGCACAAG
1081   GCCAGAGTTC TCGCTGAGGC CATGAGCCAG ACAAACTCAG GCAATATCAT GATGCAGAGG
1141   AGTAACTTTA AGGGTCCCAG GAGAATCGTC AAGTGCTTCA ATTGTGGCAA GGAGGGTCAC
1201   ATTGCCAGGA ACTGCCGCGC CCCCAGGAAG AAAGGCTGCT GGAAGTGTGG CAAAGAGGGC
1261   CACCAGATGA AGGATTGCAC CGAGCGCCAA GCAAACTTCC TGGGAAAGAT TTGGCCCAGT
1321   CATAAGGGCC GCCCTGGCGA ATTCTGCGGC AAGAAGGCCA TCGGCACCGT GCTGGTGGGC
1381   CCCACCCCCG TGAACATCAT CGGCCGGAAC ATGCTGACCC AGCTGGGCTG CACCCTGAAC
1441   TTCCCCATCA GCCCCATCGA GACCGTGCCC GTGAAGCTGA AGCCCGGCAT GGACGGCCCC
1501   AAGGTGAAGC AGTGGCCCCT GACCGAGGTG AAGATCAAGG CCCTGACCGC CATCTGCGAG
1561   GAGATGGAGA AGGAGGGCAA GATCACCAAG ATCGGCCCCG AGAACCCCTA CAACACCCCC
1621   ATCTTCGCCA TCAAGAAGGA GGACAGCACC AAGTGGCGGA AGCTGGTGGA CTTCCGGGAG
1681   CTGAACAAGC GGACCCAGGA CTTCTGGGAG GTGCAGCTGG GCATCCCCCA CCCCGCCGGC
1741   CTGAAGAAGA AGAAGAGCGT GACCGTGCTG GACGTGGGCG ACGCCTACTT CAGCGTGCCC
```

Fig. 10

```
1801   CTGGACGAGG GCTTCCGGAA GTACACCGCC TTCACCATCC CCAGCATCAA CAACGAGACC
1861   CCCGGCATCC GGTACCAGTA CAACGTGCTG CCCCAGGGCT GGAAGGGCAG CCCCGCCATC
1921   TTCCAGGCCA GCATGACCAA GATCCTGGAG CCCTTCCGGG CCAAGAACCC CGAGATCGTG
1981   ATCTACCAGT ACATGGCCGC CCTGTACGTG GGCAGCGACC TGGAGATCGG CCAGCACCGG
2041   GCCAAGATCG AGGAGCTGCG GGAGCACCTG CTGAAGTGGG GCTTCACCAC CCCCGACAAG
2101   AAGCACCAGA AGGAGCCCCC CTTCCTGTGG ATGGGCTACG AGCTGCACCC CGACAAGTGG
2161   ACCGTGCAGC CCATCCAGCT GCCCGAGAAG GACAGCTGGA CCGTGAACGA CATCCAGAAG
2221   CTGGTGGGCA AGCTGAACTG GACCAGCCAG ATCTACCCCG GCATCAAGGT GCGGCAGCTG
2281   TGCAAGCTGC TGCGGGGCAC CAAGGCCCTG ACCGACATCG TGCCCCTGAC CGAGGAGGCC
2341   GAGCTGGAGC TGGCCGAGAA CCGGGAGATC CTGAAGGAGC CCGTGCACGG CGTGTACTAC
2401   GACCCCAGCA AGGACCTGAT CGCCGAGATC CAGAAGCAGG GCGACGACCA GTGGACCTAC
2461   CAGATCTACC AGGAGCCCTT CAAGAACCTG AAAACCGGCA AGTACGCCAA GCGGCGGACC
2521   ACCCACACCA ACGACGTGAA GCAGCTGACC GAGGCCGTGC AGAAGATCAG CCTGGAGAGC
2581   ATCGTGACCT GGGGCAAGAC CCCCAAGTTC CGGCTGCCCA TCCAGAAGGA GACCTGGGAG
2641   ATCTGGTGGA CCGACTACTG GCAGGCCACC TGGATCCCCG AGTGGGAGTT CGTGAACAGC
2701   GGCCGCAAGC TTGCCACCAT GGTGGGCATC AGCTACGGCC GCAAGAAGCG CCGCCAGCGC
2761   CGCAGCACCC CGCCCAGCAG CGAGGACCAC CAGAACCCCA TCAGCAAGCA GCCCCTGCCC
2821   CAGACCCGCG GCGACCCCAC CGGCAGCGAG GAGAGCAAGA AGAAGGTGGA GAGCAAGACC
2881   AAGACCGACC CCTTCGACTG CAAGTACTGC AGCTACCACT GTCTGGTGTG CTTCCAGACC
2941   AAGGGCCTGG GCATCTCCTA CGGGCGCAAG AAACGGATGG AGCCCATCGA CCCCAACCTG
3001   GAGCCCTGGA ACCACCCCGG CAGCCAGCCC AACACCCCCT GCAACAAGTG CTACTGCAAA
3061   TACTGCTCCT ACCACTGCCT CGTGGTGGGC TGGCCCGCCG TGCGCGAGCG CATCCGCCGC
3121   ACCGAGCCCG CCGCCGAGGG CGTGGGCCCC GCCAGCCAGG ACCTGGACAA GCACGGCGCC
3181   CTGACCAGCA GCAACACCGC CCACAACAAC CCCGACTGCG CCTGGCTGCA GGCCCAGGAG
3241   GAGGAGGAGG ACGTGGGCTT CCCCGTGCGC CCCCAGGTGC CCCTGCGCCC CATGACCTAC
3301   AAGGCCGCCT TCGACCTGAG CTTCTTCCTG AAGGAGAAGG GCGGCCTGGA GGGCCTGATC
3361   CACAGCAAGC GCCGCCAGGA CATCCTGGAC CTGTGGGTGT ACCACACCCA GGGCTACTTC
3421   CCCGACTGGC AGAACTACAC CCCCGGCCCC GGCGTGCGCT ACCCCCTGAC CTTCGGCTGG
3481   TGCTTCAAGC TGGTGCCCGT GGACCCCCGC GAGGTGGAGG AGGCCAACAA GGGCGAGAAC
3541   AACTGCCTGC TGCACCCCAT GAGCCAGCAC GGCATGGAGG ACGCCGACCG CGAGGTGCTG
3601   CGCTGGGTGT TCGACAGCAG CCTGGCCCGC CGCCACCTGG CCCGCGAGAA GCACCCCGAG
3661   TACTACAAGG ACTGAGAATT CTCTAGA
```

Fig. 10 (Continued)

SEQ: PCV-1: 1783 bp

```
ORIGIN
1      ACTAGTCTCG ACATTGGTGT GGGTATTTAA ATGGAGCCAC AGCTGGTTTC TTTTATTATT
61     TGGCTGGAAC CAATCAATTG TTTGGTCCAG CTCAGGTTTG GGGGTGAAGT ACCTGGAGTG
121    GTAGGTAAAG GGCTGCCTTA TGGTGTGGCG GGAGGAGTAG TTAATATAGG GGTCATAGGC
181    CAAGTTGGTG GAGGGGGTTA CAAAGTTGGC ATCCAAGATA ACAGCAGTGG ACCCAACACC
241    TCTTTGATTA GAGGTGATGG GGTCTCTGGG GTAAAATTCA TATTTAGCCT TTCTAATACG
301    GTAGTATTGG AAAGGTAGGG GTAGGGGGTT GGTGCCGCCT GAGGGGGGGA GGAACTGGCC
361    GATGTTGAAT CTGAGCTGGT TAACATTCCA AGATGGCTGC GAGTGTCCTC CTTCTATGGT
421    GAGTACAAAT TCTCTAGAAA GGCGGCAATT GAAGATACCC GTCTTTCGGC GCCATCTGTA
481    ACGGTTTCTG AAGGCGGGGT GTGCCAAATA TGGTCTTCTG CGGAGGATGT TTCCAAGATG
541    GCTGCGGGGG CGGGTCCTTC TTCTGCGGTA ACGCCTCCTT GGCCACGTCA TCCTATAAAA
601    GTGAAAGAAG TGCGCTGCTG TAGTATTACC AGCGCACTTC GGCAGCGGCA GCACCTCGGC
661    AGCGTCGGTG AAAATGCCAA GCAAGAAAAG CGGCCCGCAA CCCCATAAGA GGTGGGTGTT
721    CACCCTTAAT AATCCTTCCG AGGAGGAGAA AAACAAAATA CGGGAGCTTC CAATCTCCCT
781    TTTTGATTAT TTTGTTTGCG GAGAGGAAGG TTTGGAAGAG GGTAGAACTC CTCACCTCCA
841    GGGGTTTGCG AATTTTGCTA AGAAGCAGAC TTTTAACAAG GTGAAGTGGT ATTTTGGTGC
901    CCGCTGCCAC ATCGAGAAAG CGAAAGGAAC CGACCAGCAG AATAAAGAAT ACTGCAGCTG
961    CAGTAAAGAA GGCCACATAC TTATCGAGTG TGGAGCTCCG CGGAACCAGG GGAAGCGCAG
1021   CGACCTGTCT ACTGCTGTGA GTACCCTTTT GGAGACGGGG TCTTTGGTGA CTGTAGCCGA
```

Fig. 11

```
1081   GCAGTTCCCT GTAACGTATG TGAGAAATTT CCGCGGGCTG GCTGAACTTT TGAAAGTGAG
1141   CGGGAAGATG CAGCAGCGTG ATTGGAAGAC AGCTGTACAC GTCATAGTGG GCCCGCCCGG
1201   TTGTGGGAAG AGCCAGTGGG CCCGTAATTT TGCTGAGCCT AGCGACACCT ACTGGAAGCC
1261   TAGTAGAAAT AAGTGGTGGG ATGGATATCA TGGAGAAGAA GTTGTTGTTT TGGATGATTT
1321   TTATGGCTGG TTACCTTGGG ATGATCTACT GAGACTGTGT GACCGGTATC CATTGACTGT
1381   AGAGACTAAA GGGGGTACTG TTCCTTTTTT GGCCCGCAGT ATTTTGATTA CCAGCAATCA
1441   GGCCCCCCAG GAATGGTACT CCTCAACTGC TGTCCCAGCT GTAGAAGCTC TCTATCGGAG
1501   GATTACTACT TTGCAATTTT GGAAGACTGC TGGAGAACAA TCCACGGAGG TACCCGAAGG
1561   CCGATTTGAA GCAGTGGACC CACCCTGTGC CCTTTTCCCA TATAAAATAA ATTACTGAGT
1621   CTTTTTTGTT ATCACATCGT AATGGTTTTT ATTTTTATTC ATTTAGAGGG TCTTTTAGGA
1681   TAAATTCTCT GAATTGTACA TAAATAGTCA GCCTTACCAC ATAATTTTGG GCTGTGGCTG
1741   CATTTTGGAG CGCATAGCCG AGGCCTGTGT GACAATCACT AGT
```

Fig. 11 (Continued)

```
SEQ: Rev. comp. PCV-1: 1783 bp

ORIGIN

1      ACTAGTGATT GTCACACAGG CCTCGGCTAT GCGCTCCAAA ATGCAGCCAC AGCCCAAAAT
61     TATGTGGTAA GGCTGACTAT TTATGTACAA TTCAGAGAAT TTATCCTAAA AGACCCTCTA
121    AATGAATAAA AATAAAAACC ATTACGATGT GATAACAAAA AAGACTCAGT AATTTATTTT
181    ATATGGGAAA AGGGCACAGG GTGGGTCCAC TGCTTCAAAT CGGCCTTCGG GTACCTCCGT
241    GGATTGTTCT CCAGCAGTCT TCCAAAATTG CAAAGTAGTA ATCCTCCGAT AGAGAGCTTC
301    TACAGCTGGG ACAGCAGTTG AGGAGTACCA TTCCTGGGGG GCCTGATTGC TGGTAATCAA
361    AATACTGCGG GCCAAAAAAG GAACAGTACC CCCTTTAGTC TCTACAGTCA ATGGATACCG
421    GTCACACAGT CTCAGTAGAT CATCCCAAGG TAACCAGCCA TAAAAATCAT CCAAAACAAC
481    AACTTCTTCT CCATGATATC CATCCCACCA CTTATTTCTA CTAGGCTTCC AGTAGGTGTC
541    GCTAGGCTCA GCAAAATTAC GGGCCCACTG GCTCTTCCCA CAACCGGGCG GGCCCACTAT
601    GACGTGTACA GCTGTCTTCC AATCACGCTG CTGCATCTTC CCGCTCACTT TCAAAAGTTC
661    AGCCAGCCCG CGGAAATTTC TCACATACGT TACAGGGAAC TGCTCGGCTA CAGTCACCAA
721    AGACCCCGTC TCCAAAAGGG TACTCACAGC AGTAGACAGG TCGCTGCGCT TCCCCTGGTT
781    CCGCGGAGCT CCACACTCGA TAAGTATGTG GCCTTCTTTA CTGCAGCTGC AGTATTCTTT
841    ATTCTGCTGG TCGGTTCCTT TCGCTTTCTC GATGTGGCAG CGGGCACCAA AATACCACTT
901    CACCTTGTTA AAAGTCTGCT TCTTAGCAAA ATTCGCAAAC CCCTGGAGGT GAGGAGTTCT
961    ACCCTCTTCC AAACCTTCCT CTCCGCAAAC AAAATAATCA AAAAGGGAGA TTGGAAGCTC
1021   CCGTATTTTG TTTTTCTCCT CCTCGGAAGG ATTATTAAGG GTGAACACCC ACCTCTTATG
1081   GGGTTGCGGG CCGCTTTTCT TGCTTGGCAT TTTCACCGAC GCTGCCGAGG TGCTGCCGCT
1141   GCCGAAGTGC GCTGGTAATA CTACAGCAGC GCACTTCTTT CACTTTTATA GGATGACGTG
1201   GCCAAGGAGG CGTTACCGCA GAAGAAGGAC CCGCCCCCGC AGCCATCTTG GAAACATCCT
1261   CCGCAGAAGA CCATATTTGG CACACCCCGC CTTCAGAAAC CGTTACAGAT GGCGCCGAAA
1321   GACGGGTATC TTCAATTGCC GCCTTTCTAG AGAATTTGTA CTCACCATAG AAGGAGGACA
1381   CTCGCAGCCA TCTTGGAATG TTAACCAGCT CAGATTCAAC ATCGGCCAGT TCCTCCCCCC
1441   CTCAGGCGGC ACCAACCCCC TACCCCTACC TTTCCAATAC TACCGTATTA GAAAGGCTAA
1501   ATATGAATTT TACCCCAGAG ACCCCATCAC CTCTAATCAA AGAGGTGTTG GGTCCACTGC
1561   TGTTATCTTG GATGCCAACT TTGTAACCCC CTCCACCAAC TTGGCCTATG ACCCCTATAT
1621   TAACTACTCC TCCCGCCACA CCATAAGGCA GCCCTTTACC TACCACTCCA GGTACTTCAC
1681   CCCCAAACCT GAGCTGGACC AAACAATTGA TTGGTTCCAG CCAAATAATA AAAGAAACCA
1741   GCTGTGGCTC CATTTAAATA CCCACACCAA TGTCGAGACT AGT
```

Fig. 12

SEQ pTH -no insert: 4912 bp

ORIGIN

| | | | | | | |
|---|---|---|---|---|---|---|
| 1 | GACGGATCGG | GAGATCTCCC | GATCCCCTAT | GGTCGACTCT | CAGTACAATC | TGCTCTGATG |
| 61 | CCGCATAGTT | AAGCCAGTAT | CTGCTCCCTG | CTTGTGTGTT | GGAGGTCGCT | GAGTAGTGCG |
| 121 | CGAGCAAAAT | TTAAGCTACA | ACAAGGCAAG | GCTTGACCGA | CAATTGCATG | AAGAATCTGC |
| 181 | TTAGGGTTAG | GCGTTTTGCG | CTGCTTCGCG | ATGTACGGGC | CAGATATACG | CGTTTTGAGA |
| 241 | TTTCTGTCGC | CGACTAAATT | CATGTCGCGC | GATAGTGGTG | TTTATCGCCG | ATAGAGATGG |
| 301 | CGATATTGGA | AAAATCGATA | TTTGAAAATA | TGGCATATTG | AAAATGTCGC | CGATGTGAGT |
| 361 | TTCTGTGTAA | CTGATATCGC | CATTTTTCCA | AAAGTGATTT | TTGGGCATAC | GCGATATCTG |
| 421 | GCGATAGCGC | TTATATCGTT | TACGGGGGAT | GGCGATAGAC | GACTTTGGTG | ACTTGGGCGA |
| 481 | TTCTGTGTGT | CGCAAATATC | GCAGTTTCGA | TATAGGTGAC | AGACGATATG | AGGCTATATC |
| 541 | GCCGATAGAG | GCGACATCAA | GCTGGCACAT | GGCCAATGCA | TATCGATCTA | TACATTGAAT |
| 601 | CAATATTGGC | CATTAGCCAT | ATTATTCATT | GGTTATATAG | CATAAATCAA | TATTGGCTAT |
| 661 | TGGCCATTGC | ATACGTTGTA | TCCATATCAT | AATATGTACA | TTTATATTGG | CTCATGTCCA |
| 721 | ACATTACCGC | CATGTTGACA | TTGATTATTG | ACTAGTTATT | AATAGTAATC | AATTACGGGG |
| 781 | TCATTAGTTC | ATAGCCCATA | TATGGAGTTC | CGCGTTACAT | AACTTACGGT | AAATGGCCCG |
| 841 | CCTGGCTGAC | CGCCCAACGA | CCCCCGCCCA | TTGACGTCAA | TAATGACGTA | TGTTCCCATA |
| 901 | GTAACGCCAA | TAGGGACTTT | CCATTGACGT | CAATGGGTGG | AGTATTTACG | GTAAACTGCC |
| 961 | CACTTGGCAG | TACATCAAGT | GTATCATATG | CCAAGTACGC | CCCCTATTGA | CGTCAATGAC |
| 1021 | GGTAAATGGC | CCGCCTGGCA | TTATGCCCAG | TACATGACCT | TATGGGACTT | TCCTACTTGG |
| 1081 | CAGTACATCT | ACGTATTAGT | CATCGCTATT | ACCATGGTGA | TGCGGTTTTG | GCAGTACATC |
| 1141 | AATGGGCGTG | GATAGCGGTT | TGACTCACGG | GGATTTCCAA | GTCTCCACCC | CATTGACGTC |
| 1201 | AATGGGAGTT | TGTTTTGGCA | CCAAAATCAA | CGGGACTTTC | CAAAATGTCG | TAACAACTCC |
| 1261 | GCCCCATTGA | CGCAAATGGG | CGGTAGGCGT | GTACGGTGGG | AGGTCTATAT | AAGCAGAGCT |
| 1321 | CGTTTAGTGA | ACCGTCAGAT | CGCCTGGAGA | CGCCATCCAC | GCTGTTTTGA | CCTCCATAGA |
| 1381 | AGACACCGGG | ACCGATCCAG | CCTCCGCGGC | CGGGAACGGT | GCATTGGAAC | GCGGATTCCC |
| 1441 | CGTGCCAAGA | GTGACGTAAG | TACCGCCTAT | AGAGTCTATA | GGCCCACCCC | CTTGGCTTCT |
| 1501 | TATGCATGCT | ATACTGTTTT | TGGCTTGGGG | TCTATACACC | CCCGCTTCCT | CATGTTATAG |
| 1561 | GTGATGGTAT | AGCTTAGCCT | ATAGGTGTGG | GTTATTGACC | ATTATTGACC | ACTCCCCTAT |
| 1621 | TGGTGACGAT | ACTTTCCATT | ACTAATCCAT | AACATGGCTC | TTTGCCACAA | CTCTCTTTAT |
| 1681 | TGGCTATATG | CCAATACACT | GTCCTTCAGA | GACTGACACG | GACTCTGTAT | TTTTACAGGA |
| 1741 | TGGGGTCTCA | TTTATTATTT | ACAAATTCAC | ATATACAACA | CCACCGTCCC | CAGTGCCCGC |
| 1801 | AGTTTTTATT | AAACATAACG | TGGGATCTCC | ACGCGAATCT | CGGGTACGTG | TTCCGGACAT |
| 1861 | GGGCTCTTCT | CCGGTAGCGG | CGGAGCTTCT | ACATCCGAGC | CCTGCTCCCA | TGCCTCCAGC |
| 1921 | GACTCATGGT | CGCTCGGCAG | CTCCTTGCTC | CTAACAGTGG | AGGCCAGACT | TAGGCACAGC |
| 1981 | ACGATGCCCA | CCACCACCAG | TGTGCCGCAC | AAGGCCGTGG | CGGTAGGGTA | TGTGTCTGAA |
| 2041 | AATGAGCTCG | GGGAGCGGGC | TTGCACCGCT | GACGCATTTG | GAAGACTTAA | GGCAGCGGCA |
| 2101 | GAAGAAGATG | CAGGCAGCTG | AGTTGTTGTG | TTCTGATAAG | AGTCAGAGGT | AACTCCCGTT |
| 2161 | GCGGTGCTGT | TAACGGTGGA | GGGCAGTGTA | GTCTGAGCAG | TACTCGTTGC | TGCCGCGCGC |
| 2221 | GCCACCAGAC | ATAATAGCTG | ACAGACTAAC | AGACTGTTCC | TTTCCATGGG | TCTTTTCTGC |
| 2281 | AGTCACCGTC | CTTGACACGG | AGCTCGGTAC | CGAGCTCGGA | TCCACTAGTA | ACGGCCGCCA |
| 2341 | GTGTGCTGGA | ATTCTGCAGA | TATCCATCAC | ACTGGCGGCC | GCTCGAGCAT | GCATCTAGAG |
| 2401 | GGCCCTATTC | TATAGTGTCA | CCTAAATGCT | AGAGCTCGCT | GATCAGCCTC | GACTGTGCCT |
| 2461 | TCTAGTTGCC | AGCCATCTGT | TGTTTGCCCC | TCCCCCGTGC | CTTCCTTGAC | CCTGGAAGGT |
| 2521 | GCCACTCCCA | CTGTCCTTTC | CTAATAAAAT | GAGGAAATTG | CATCGCATTG | TCTGAGTAGG |
| 2581 | TGTCATTCTA | TTCTGGGGGG | TGGGGTGGGG | CAGGACAGCA | AGGGGGAGGA | TTGGGAAGAC |
| 2641 | AATAGCAGGC | ATGCTGGGGA | TGCGGTGGGC | TCTATGGCTT | CTGAGGCGGA | AAGAACCAGC |
| 2701 | TGGGGCTCGA | GGGGGGATCG | ATCCCGTCGA | CCTCGAGAGC | TTGGCGTAAT | CATGGTCATA |
| 2761 | GCTGTTTCCT | GTGTGAAATT | GTTATCCGCT | CACAATTCCA | CACAACATAC | GAGCCGGAAG |
| 2821 | CATAAAGTGT | AAAGCCTGGG | GTGCCTAATG | AGTGAGCTAA | CTCACATTAA | TTGCGTTGCG |
| 2881 | CTCACTGCCC | GCTTTCCAGT | CGGGAAACCT | GTCGTGCCAG | CTGCATTAAT | GAATCGGCCA |
| 2941 | ACGCGCGGGG | AGAGGCGGTT | TGCGTATTGG | GCGCTCTTCC | GCTTCCTCGC | TCACTGACTC |
| 3001 | GCTGCGCTCG | GTCGTTCGGC | TGCGGCGAGC | GGTATCAGCT | CACTCAAAGG | CGGTAATACG |
| 3061 | GTTATCCACA | GAATCAGGGG | ATAACGCAGG | AAAGAACATG | TGAGCAAAAG | GCCAGCAAAA |
| 3121 | GGCCAGGAAC | CGTAAAAAGG | CCGCGTTGCT | GGCGTTTTTC | CATAGGCTCC | GCCCCCCTGA |
| 3181 | CGAGCATCAC | AAAAATCGAC | GCTCAAGTCA | GAGGTGGCGA | AACCCGACAG | GACTATAAAG |

Fig. 13

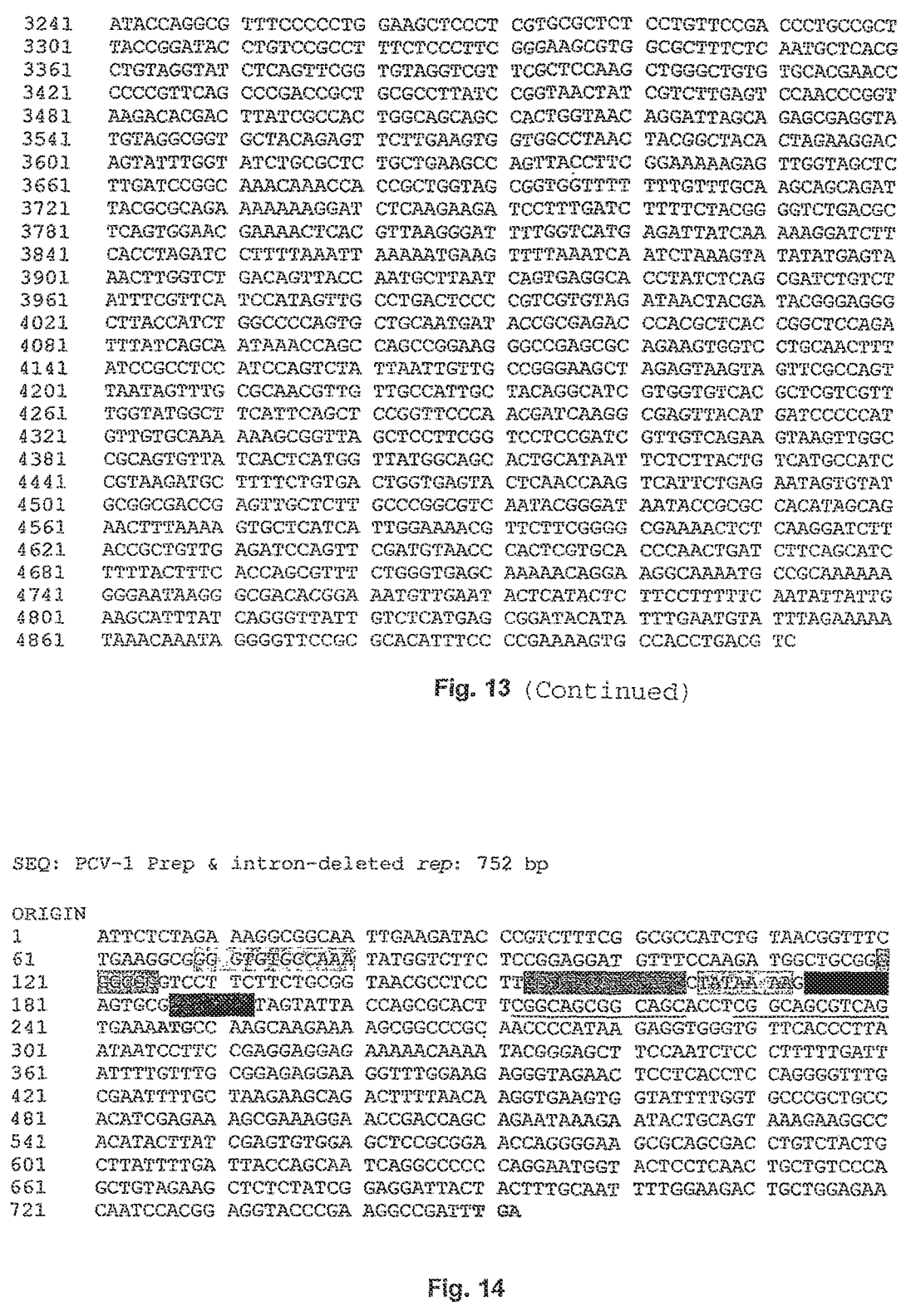

```
3241   ATACCAGGCG TTTCCCCCTG GAAGCTCCCT CGTGCGCTCT CCTGTTCCGA CCCTGCCGCT
3301   TACCGGATAC CTGTCCGCCT TTCTCCCTTC GGGAAGCGTG GCGCTTTCTC AATGCTCACG
3361   CTGTAGGTAT CTCAGTTCGG TGTAGGTCGT TCGCTCCAAG CTGGGCTGTG TGCACGAACC
3421   CCCCGTTCAG CCCGACCGCT GCGCCTTATC CGGTAACTAT CGTCTTGAGT CCAACCCGGT
3481   AAGACACGAC TTATCGCCAC TGGCAGCAGC CACTGGTAAC AGGATTAGCA GAGCGAGGTA
3541   TGTAGGCGGT GCTACAGAGT TCTTGAAGTG GTGGCCTAAC TACGGCTACA CTAGAAGGAC
3601   AGTATTTGGT ATCTGCGCTC TGCTGAAGCC AGTTACCTTC GGAAAAAGAG TTGGTAGCTC
3661   TTGATCCGGC AAACAAACCA CCGCTGGTAG CGGTGGTTTT TTTGTTTGCA AGCAGCAGAT
3721   TACGCGCAGA AAAAAAGGAT CTCAAGAAGA TCCTTTGATC TTTTCTACGG GGTCTGACGC
3781   TCAGTGGAAC GAAAACTCAC GTTAAGGGAT TTTGGTCATG AGATTATCAA AAAGGATCTT
3841   CACCTAGATC CTTTTAAATT AAAAATGAAG TTTTAAATCA ATCTAAAGTA TATATGAGTA
3901   AACTTGGTCT GACAGTTACC AATGCTTAAT CAGTGAGGCA CCTATCTCAG CGATCTGTCT
3961   ATTTCGTTCA TCCATAGTTG CCTGACTCCC CGTCGTGTAG ATAACTACGA TACGGGAGGG
4021   CTTACCATCT GGCCCCAGTG CTGCAATGAT ACCGCGAGAC CCACGCTCAC CGGCTCCAGA
4081   TTTATCAGCA ATAAACCAGC CAGCCGGAAG GGCCGAGCGC AGAAGTGGTC CTGCAACTTT
4141   ATCCGCCTCC ATCCAGTCTA TTAATTGTTG CCGGGAAGCT AGAGTAAGTA GTTCGCCAGT
4201   TAATAGTTTG CGCAACGTTG TTGCCATTGC TACAGGCATC GTGGTGTCAC GCTCGTCGTT
4261   TGGTATGGCT TCATTCAGCT CCGGTTCCCA ACGATCAAGG CGAGTTACAT GATCCCCCAT
4321   GTTGTGCAAA AAAGCGGTTA GCTCCTTCGG TCCTCCGATC GTTGTCAGAA GTAAGTTGGC
4381   CGCAGTGTTA TCACTCATGG TTATGGCAGC ACTGCATAAT TCTCTTACTG TCATGCCATC
4441   CGTAAGATGC TTTTCTGTGA CTGGTGAGTA CTCAACCAAG TCATTCTGAG AATAGTGTAT
4501   GCGGCGACCG AGTTGCTCTT GCCCGGCGTC AATACGGGAT AATACCGCGC CACATAGCAG
4561   AACTTTAAAA GTGCTCATCA TTGGAAAACG TTCTTCGGGG CGAAAACTCT CAAGGATCTT
4621   ACCGCTGTTG AGATCCAGTT CGATGTAACC CACTCGTGCA CCCAACTGAT CTTCAGCATC
4681   TTTTACTTTC ACCAGCGTTT CTGGGTGAGC AAAAACAGGA AGGCAAAATG CCGCAAAAAA
4741   GGGAATAAGG GCGACACGGA AATGTTGAAT ACTCATACTC TTCCTTTTTC AATATTATTG
4801   AAGCATTTAT CAGGGTTATT GTCTCATGAG CGGATACATA TTTGAATGTA TTTAGAAAAA
4861   TAAACAAATA GGGGTTCCGC GCACATTTCC CCGAAAAGTG CCACCTGACG TC
```

Fig. 13 (Continued)

SEQ: PCV-1 Prep & intron-deleted *rep*: 752 bp

```
ORIGIN
1      ATTCTCTAGA AAGGCGGCAA TTGAAGATAC CCGTCTTTCG GCGCCATCTG TAACGGTTTC
61     TGAAGGCGGG GTGTGGCAAA TATGGTCTTC TCCGGAGGAT GTTTCCAAGA TGGCTGCGG[illegible]
121    [illegible]GTCCT TCTTCTGCGG TAACGCCTCC TT[illegible]CTATAA AAG[illegible]
181    AGTGCG[illegible]TAGTATTA CCAGCGCACT TCGGCAGCGG CAGCACCTCG GCAGCGTCAG
241    TGAAAATGCC AAGCAAGAAA AGCGGCCCGC AACCCCATAA GAGGTGGGTG TTCACCCTTA
301    ATAATCCTTC CGAGGAGGAG AAAAACAAAA TACGGGAGCT TCCAATCTCC CTTTTTGATT
361    ATTTTGTTTG CGGAGAGGAA GGTTTGGAAG AGGGTAGAAC TCCTCACCTC CAGGGGTTTG
421    CGAATTTTGC TAAGAAGCAG ACTTTTAACA AGGTGAAGTG GTATTTTGGT GCCCGCTGCC
481    ACATCGAGAA AGCGAAAGGA ACCGACCAGC AGAATAAAGA ATACTGCAGT AAAGAAGGCC
541    ACATACTTAT CGAGTGTGGA GCTCCGCGGA ACCAGGGGAA GCGCAGCGAC CTGTCTACTG
601    CTTATTTTGA TTACCAGCAA TCAGGCCCCC CAGGAATGGT ACTCCTCAAC TGCTGTCCCA
661    GCTGTAGAAG CTCTCTATCG GAGGATTACT ACTTTGCAAT TTTGGAAGAC TGCTGGAGAA
721    CAATCCACGG AGGTACCCGA AGGCCGATTT GA
```

Fig. 14

SEQ: PCV-1 truncated Prep /*rep*: 150 bp

ORIGIN
1 ATTCTCTAGA AAGGCGGCAA TTGAAGATAC CCGTCTTTCG GCGCCATCTG TAACGGTTTC
61 TGAAGGCGGG GTGTGCCAAA TATGGTCTTC TCCGGAGGAT GTTTCCAAGA TGGCTGCGGG
121 GGCGGGTCCT TCTTCTGCGG TAACGCCTCC TT[redacted]CTATAA AAG[redacted]
181 AGTGCG[redacted]TAGTATTA CCAGCGCACT TCGGCAG//A TCAGGCCCCC CAGGAATGGT
139 ACTCCTCAAC TGCTGTCCCA GCTGTAGAAG CTCTCTATCG GAGGATTACT ACTTTGCAAT
199 TTTGGAAGAC TGCTGGAGAA CAATCCACGG AGGTACCCGA AGGCCGATTT GA

Fig. 15

Alignment of selected circovirus DNA sequences equivalent to PCV-1 PcapR region

```
pcv-1            ---CTGTAGC CGAGCAGTTC CCTGTAACGT ATGTGAGAAA TTTCCGCGGG
pcv-2            ---CCGTTGC AGAGCAGCAC CCTGTAACGT TTGTCAGAAA TTTCCGCGGG
BFDV-AFG         -------CGC GCGAGAGTTC CCAGATATCT ACGTCAGGCA TGGGCGGGGC
canary_cv        -------CGC GCGAGAGTTC AGTGAGATCT ACGTCAAGTA TGGGCGTGGT
columbid_cv      ------TCGC GCGAGACTTC AGTGAGATAT ACGTCAAGTA TGGGCGTGGC
duck_circovirus  -TGAGGTGGC CCGGAAGTTC CCCACGACTT ATGTTATCTT TGGGCGTGGC
finch_circovirus ------TCGC GCGAGAGTTC AGTCTAGCCT ACGTCAGATA TGGGCGGGGC
goose_circovirus ------TGGC CCGGAAGTAC CCGACGACTT ATGTAATGTT TGGGCGGGGC
gull_circovirus  GTGAAATCGC GCGAGAGTTC AGTGAAGTCT ACGTCAAGTA TGGGCGGGGC

pcv-1            CTGGCTGAAC TTTTGAAAGT GAGCGGGAAG ATGCAGCAGC GTGATTGGAA
pcv-2_           CTGGCTGAAC TTTTGAAAGT GAGCGGGAAA ATGCAGAAGC GTGATTGGAA
BFDV-AFG         TTACATAATC TCTCGCTAAT GGTTGGTTCC CGGCCA---C GTGACTTCAA
canary_cv        CTGAGGGATT TGGCCCTGAT GATTGGACAG AAACCC---C GTGACTTCAA
columbid_cv      TTGCGCGACC TGAAGCTGCT GATTGGTCAG CAGCCT---C GTGACTTCAA
duck_circovirus  CTGGAACGCC TCCGTCACCT GATCGTTGAG ACGCAA---C GTGATTGGAA
finch_circovirus CTGCGTGATC TTGCGCTGCT GATTGGCCAG AAGCCC---C GTGACTTCAA
goose_circovirus TTAGAGCGGT TGCGTCAGCT GATCGTGGAG ACCGCT---C GTGATTGGAA
gull_circovirus  CTCCGTGATC TCCGGTTGCT GATTGGTTGC CCGCCC---C GCGATTTCAA

pcv-1            GACAGCTGTA CACGTCATAG TGGGCCCGCC CGGTTGTGGG AAGAGCCAGT
pcv-2            GACTAATGTA CACGTCATTG TGGGGCCACC TGGGTGTGGT AAAAGCAAAT
BFDV-AFG         GACTGAGGTC GACGTCATCT ACGGACCACC GGGGTGTGGC AAGAGTAGAT
canary_cv        GACGGAAGTC GTCGTCATCA CAGGGCCTTC CGGGGTGGGC AAGTCCCGAC
columbid_cv      AACGGAAGTC ATCGTCATCA CGGGCCCGCC CGGTTGCGGG AAGAGCCGTT
duck_circovirus  GACCGAAGTC ATCGTTCTGA TTGGTCCGCC CGGCACCGGG AAGAGCCGTT
finch_circovirus AACGGAAGTC ATAGTGCTGA CCGGCCCTAG TGGGTGTGGC AAATCCCGCT
goose_circovirus GACGGAGGTC ATCGTTCTGA TTGGGCGGCC TGGAAGCGGG AAGAGCCGTT
gull_circovirus  AACAGAAGTC ATCGTTCTGA TTGGCCCACC TGGCTGTGGC AAGTCAAAAT

pcv-1            GGGCCCGTAA TTTTGCTGAG CCTAGCGACA CCTACTGGAA GCC-
pcv-2            GGGCTGCTAA TTTTGCAGAC CCGGAAACCA CATACTGGAA ACC-
BFDV-AFG         GGGCCAATGA GCAGCCGG-- -GGACCAAAT ATTATAAAAT GCG-
canary_cv        TTGCCTCTGA AATGGAAG-- -GATCGAAGT TCTACAAG-- ----
columbid_cv      GGGCAGCTGA GTACCCCG-- -GAAGTAAAT TTTACAAGAT GA--
duck_circovirus  ATGCATTTGA ATTTCCCGCC GAAAACAAGT ATTACAAACC ACGC
finch_circovirus GGGCCAATGA ACAAGAAG-- -GAACTAAGT TTTATAAAAT GA--
goose_circovirus ACGCGTTTGA ATTTCCCGCG CGTGAAAAGT ATTATAAAT- ----
gull_circovirus  TGGCCAATGA GATGGAAG-- -GGTCTAAGT TCTACA---- ----
```

Fig. 16 (a)

Reverse complementary DNA sequences of selected circoviruses. Displayed sequences are equivalent to to PCV-1 Pcap sequence.

PCV-1
GGCTTCCAGT AGGTGTCGCT AGGCTCAGCA AAATTACGGG CCCACTGGCT CTTCCCACAA
CCGGGCGGGC CCACTATGAC GTGTACAGCT GTCTTCCAAT CACGCTGCTG CATCTTCCCG
CTCACTTTCA AAAGTTCAGC CAGCCCGCGG AAATTTCTCA CATACGTTAC AGGGAACTGC
TCGGCTACAG

PCV-2
GGTTTCCAGT ATGTGGTTTC CGGGTCTGCA AAATTAGCAG CCCATTTGCT TTTACCACAC
CCAGGTGGCC CCACAATGAC GTGTACATTA GTCTTCCAAT CACGCTTCTG CATTTTCCCG
CTCACTTTCA AAAGTTCAGC CAGCCCGCGG AAATTTCTGA CAAACGTTAC AGGGTGCTGC
TCTGCAACGG

BFDV-AFG
GGTTTCCAGT ATGTGGTTTC CGGGTCTGCA AAATTAGCAG CCCATTTGCT TTTACCACAC
CCAGGTGGCC CCACAATGAC GTGTACATTA GTCTTCCAAT CACGCTTCTG CATTTTCCCG
CTCACTTTCA AAAGTTCAGC CAGCCCGCGG AAATTTCTGA CAAACGTTAC AGGGTGCTGC
TCTGCAACGG

Canary cv
CTTGTAGAAC TTCGATCCTT CCATTTCAGA GGCAAGTCGG GACTTGCCCA CCCCGGAAGG
CCCTGTGATG ACGACGACTT CCGTCTTGAA GTCACGGGGT TTCTGTCCAA TCATCAGGGC
CAAATCCCTC AGACCACGCC CATACTTGAC GTAGATCTCA CTGAACTCTC GCGCG

Columbid cv
TCATCTTGTA AAATTTACTT CCGGGGTACT CAGCTGCCCA ACGGCTCTTC CCGCAACCGG
GCGGGCCCGT GATGACGATG ACTTCCGTTT TGAAGTCACG AGGCTGCTGA CCAATCAGCA
GCTTCAGGTC GCGCAAGCCA CGCCCATACT TGACGTATAT CTCACTGAAG TCTCGCGCGA

Duck cv
GCGTGGTTTG TAATACTTGT TTTCGGCGGG AAATTCAAAT GCATAACGGC TCTTCCCGGT
GCCGGGCGGA CCAATCAGAA CGATGACTTC GGTCTTCCAA TCACGTTGCG TCTCAACGAT
CAGGTGACGG AGGCGTTCCA GGCCACGCCC AAAGATAACA TAAGTCGTGG GGAACTTCCG
GGCCACCTCA

Finch cv
TCATTTTATA AAACTTAGTT CCTTCTTGTT CATTGGCCCA GCGGGATTTG CCACACCCAC
TAGGGCCGGT CAGCACTATG ACTTCCGTTT TGAAGTCACG GGGCTTCTGG CCAATCAGCA
GCGCAAGATC ACGCAGGCCC CGCCCATATC TGACGTAGGC TAGACTGAAC TCTCGCGCGA

Goose cv
ATTTATAATA CTTTTCACGC GCGGGAAATT CAAACGCGTA ACGGCTCTTC CCGCTTCCAG
GCCGCCCAAT CAGAACGATG ACCTCCGTCT TCCAATCACG AGCGGTCTCC ACGATCAGCT
GACGCAACCG CTCTAAGCCC CGCCCAAACA TTACATAAGT CGTCGGGTAC TTCCGGGCCA

Gull cv
TGTAGAACTT AGACCCTTCC ATCTCATTGG CCAATTTTGA CTTGCCACAG CCAGGTGGGC
CAATCAGAAC GATGACTTCT GTTTTGAAAT CGCGGGGCGG GCAACCAATC AGCAACCGGA
GATCACGGAG GCCCCGCCCA TACTTGACGT AGACTTCACT GAACTCTCGC GCGATTTCAC

Fig. 16 (b)

1. PCV-1 Pcap region

```
              GCAGTTCCCT GTAACGTATG TGAGAAATTT CCGCGGGCTG  entry         score
                             <----------                    M00147 HSF2  91.0
                                        ---------->         M00147 HSF2  88.5
                                        ---------->         M00146 HSF1  87.3
                                      <----------           M00074 c-Ets- 86.6

451 GCTGAACTTT TGAAAGTGAG CGGGAAGATG CAGCAGCGTG ATTGGAAGAC  entry         score
                                       ----------->         M00075 GATA-1 92.2
    -------->                                               M00109 C/EBPb 85.5

501 AGCTGTACAC GTCATAGTGG GCCCGCCCGG TTGTGGGAAG AGCCAGTGGG  entry         score
                           <----------                      M00223 STATx  88.5
    <--------                                               M00039 CREB   87.6

    551 CCCGTAATTT TGCTGAGCCT AGCGACACCT ACTGGAAGCC          entry         score
                                         -------->          M00032 c-Ets- 89.2
        <--------                                           M00101 CdxA   85.7
```

Fig. 17 (a)

2. PCV-2 Pcap region

```
                CAGA GCAGCACCCT GTAACGTTTG TCAGAAATTT CCGCGGGCTG  entry         score
                                  <-------                        M00101 CdxA   93.6
                                  <-----------                    M00147 HSF2   91.0
                                  <-------->                      M00100 CdxA   89.7
                                             ---------->          M00147 HSF2   88.5
                                             ---------->          M00146 HSF1   87.3
                                           <----------            M00074 c-Ets- 86.6

451 GCTGAACTTT TGAAAGTGAG CGGGAAAATG CAGAAGCGTG ATTGGAAGAC  entry         score
                                       ----------->         M00075 GATA-1 92.2
                            <--------                       M00050 E2F    90.8
                                        --                  M00101 CdxA   86.4
    ---------->                                             M00109 C/EBPb 85.5

501 TAATGTACAC GTCATTGTGG GGCCACCTGG GTGTGGTAAA AGCAAATGGG  entry         score
                              -------->                     M00271 AML-1a 100.0
    <-----------                                            M00251 XBP-1  88.0
                                        ---------->         M00159 C/EBP  87.7
                   <--------                                M00039 CREB   87.6
    -------->                                               M00101 CdxA   86.4
                                         -------->          M00148 SRY    86.4
        <---------                                          M00162 Oct-1  85.7

551 CTGCTAATTT TGCAGACCCG GAAACCACAT ACTGGAAACC             entry         score
                   <--------                                M00271 AML-1a 100.0
    ---------->                                             M00032 c-Ets- 86.3
```

Fig. 17 (b)

3. Beak and feather disease virus (African grey) - BFDV-AFG

```
                CGAGAG TTCCCAGATA  entry         score
                --------            M00076 GATA-2 90.1
              <-----------          M00087 Ik-2   89.5
                --------            M00075 GATA-1 86.9
              <--------             M00050 E2F    86.2
```

Fig. 17 (c)

```
                                                       ---  M00157 RORalp 86.2
                                         <----------        M00147 HSF2   85.9

401 TCTACGTCAG GCATGGGCGG GGCTTACATA ATCTCTCGCT AATGGTTGGT  entry         score
      <-------                                              M00039 CREB   91.6
                            <------------                   M00045 E4BP4  90.7
                             ----------->                   M00228 VBP    90.7
     -->                                                    M00076 GATA-2 90.1
                  ---------->                               M00008 Sp1    89.0
                              -------->                     M00040 CRE-BP 89.0
                           <---------------                 M00109 C/EBPb 88.7
                             ----------->                   M00260 HLF    88.2
     -->                                                    M00075 GATA-1 86.9
                              <--------                     M00040 CRE-BP 86.7
     --------->                                             M00157 RORalp 86.2
                                 <---------                 M00077 GATA-3 85.9
                                 <--------                  M00101 CdxA   85.7

451 TCCCGGCCAC GTGACTTCAA GACTGAGGTC GACGTCATCT ACGGACCACC  entry         score
        -------->                                           M00217 USF    97.9
     <----------------                                      M00236 Arnt   95.1
      --------------->                                      M00121 USF    94.5
      <---------------                                      M00121 USF    94.5
      --------------->                                      M00122 USF    94.2
      <---------------                                      M00122 USF    94.2
                                <--------                   M00039 CREB   93.6
        <-------                                            M00217 USF    93.2
                                <------------               M00113 CREB   91.8
                          ----->                            M00271 AML-1a 88.7
       ------------->                                       M00055 N-Myc  88.7
      --------------->                                      M00119 Max    87.9
      <---------------                                      M00119 Max    87.9
               ------->                                     M00041 CRE-BP 87.2
                                <--------                   M00041 CRE-BP 87.2
                                -------->                   M00041 CRE-BP 86.9
               <------                                      M00041 CRE-BP 86.2
               ------->                                     M00039 CREB   86.1
       <-----------                                         M00055 N-Myc  85.9
               <-------                                     M00039 CREB   85.6
                                -------->                   M00039 CREB   85.6

501 GGGGTGTGGC AAGAGTAGAT GGGCCAATGA GCAGCCGGGG ACCAAATATT  entry         score
                                                      <     M00101 CdxA   92.9
                                                   ----     M00101 CdxA   91.4
                                                   <---     M00101 CdxA   91.4
                                                     --     M00252 TATA   91.4
                 ---------->                                M00075 GATA-1 87.3
                                                      <     M00100 CdxA   87.2
                                         <-----------       M00131 HNF-3b 86.1
                                                    ---     M00216 TATA   85.5
                                     --------->             M00083 MZF1   85.2
```

Fig. 17 (c) (Continued)

4. Canary circovirus

```
                                     TGGTGGAGAT CGCGCGAGAG entry         core
                                     ---------->           M00075 GATA-1 90.2
                                     ---------->           M00076 GATA-2 89.7
                                           <-------        M00050 E2F    86.2
                                      --------->           M00077 GATA-3 85.0

351 TTCAGTGAGA TCTACGTCAA GTATGGGCGT GGTCTGAGGG ATTTGGCCCT entry         score
```

Fig. 17 (d)

```
                <--------                                     M00039 CREB    91.6
                              ------------>                   M00008 Sp1     89.0
                     -------->                                M00240 Nkx-2.  88.4
                                                         ---  M00075 GATA-1  88.2
                                                   -------->  M00050 E2F     86.2

401 GATGATTGGA CAGAAACCCC GTGACTTCAA GACGGAAGTC GTCGTCATCA entry       score
                                 ------------------>          M00025 Elk-1   88.7
    ------->                                                  M00075 GATA-1  88.2
    --------->                                                M00075 GATA-1  87.8
                                                <-----------  M00113 CREB    87.7
                            ------->                          M00041 CRE-BP  87.2
                     -------->                                M00217 USF     86.6
                            <-------                          M00041 CRE-BP  86.2
                            ------->                          M00039 CREB    86.1
                            <-------                          M00039 CREB    85.6

451 CAGGGCCTTC CGGGGTGGGC AAGTCCCGAC TTGCCTCTGA AATGGAAGGA entry       score
                                                    --------  M00147 HSF2    92.9
                     <----------                              M00054 NF-kap  91.3
      <----------------                                       M00025 Elk-1   88.3
    -                                                         M00113 CREB    87.7
       <----------                                            M00032 c-Ets-  86.3
       <----------                                            M00108 NRF-2   86.0
                     <-------------                           M00208 NF-kap  85.7
                      <----------                             M00052 NF-kap  85.4
                                                    --------  M00146 HSF1    85.1
     ------------>                                            M00053 c-Rel   85.1

501 TCGAAGTTCT                                               entry       score
    -->                                                       M00147 HSF2    92.9
    -->                                                       M00146 HSF1    85.1
```

Fig. 17 (d) (Continued)

5. Columbid circovirus

```
                TCGCGCGAGA CTTCAGTGAG ATATACGTCA AGTATGGGCG entry       score
                                      <--------               M00039 CREB    93.1
                                           ------->           M00240 Nkx-2.  88.4

501 TGGCTTGCGC GACCTGAAGC TGCTGATTGG TCAGCAGCCT CGTGACTTCA entry       score
                          ------------>                       M00075 GATA-1  93.5
                                                          -   M00074 c-Ets-  90.5
                                                         --   M00025 Elk-1   90.0
                          ----------------->                  M00209 NF-Y    89.6
                                                  -------->   M00041 CRE-BP  87.2
                           <----------                        M00096 Pbx-1   86.3
                                                  <-------    M00041 CRE-BP  86.2
                                                  -------->   M00039 CREB    86.1
                                                         --   M00003 v-Myb   85.9
                                                  <-------    M00039 CREB    85.6

551 AAACGGAAGT CATCGTCATC ACGGGCCCGC CCGGTTGCGG GAAGAGCCGT entry       score
                                                       <----  M00227 v-Myb   96.8
                                         <----------          M00223 STATx   92.3
                <-----------                                  M00075 GATA-1  91.0
    -------------->                                           M00074 c-Ets-  90.5
    -------------->                                           M00025 Elk-1   90.0
     ----------->                                             M00108 NRF-2   87.7
     ----------->                                             M00032 c-Ets-  86.3
    -------->                                                 M00003 v-Myb   85.9

601 TGGCAGCTG AGTACCCCGG AAGTAAATTT TACA                      entry       score
```

Fig. 17 (e)

```
   ----                                                       M00227 v-Myb  96.8
                     ----------->                             M00032 c-Ets- 95.1
                   --------------->                           M00074 c-Ets- 90.9
                  ---------------->                           M00025 Elk-1  90.4
```

Fig. 17 (e) (Continued)

6. Duck circovirus

```
                                      TGAGGTGGCC CGGAAGTTCC entry    score
                                                       <--  M00083 MZF1   95.7
                                       ---------------->    M00025 Elk-1  92.6
                                          ----------->      M00032 c-Ets- 92.2
                                              <---------    M00054 NF-kap 91.6
                                        ---------------->   M00074 c-Ets- 90.1
                                              <---------    M00053 c-Rel  89.3
                                              <---------    M00052 NF-kap 88.7
                                             ---------->    M00053 c-Rel  86.8
                                          ------------>     M00108 NRF-2  86.0

401 CCACGACTTA TGTTATCTTT GGGCGTGGCC TGGAACGCCT CCGTCACCTG entry     score
    -----                                                 M00083 MZF1   95.7
    -                                                     M00054 NF-kap 91.6
                                                     ---- M00075 GATA-1 90.6
           <-----------                                   M00080 Evi-1  90.4
                                               <--------- M00220 SREBP- 89.8
           <-----------                                   M00082 Evi-1  89.8
                                              ----------- M00073 deltaE 89.6
           <-----------                                   M00079 Evi-1  89.4
    -                                                     M00053 c-Rel  89.3
    -                                                     M00052 NF-kap 88.7
                                              <---------- M00001 MyoD   88.4
         -------->                                        M00101 CdxA   86.4
                                              ----------- M00220 SREBP- 85.9
                                             ------------ M00122 USF    85.3
                                             <----------- M00122 USF    85.3

451 ATCGTTGAGA CGCAACGTGA TTGGAAGACC GAAGTCATCG TTCTGATTGG entry     score
                    ------------>                         M00075 GATA-1 92.2
    ------>                                               M00075 GATA-1 90.6
    ---                                                   M00220 SREBP- 89.8
    ->                                                    M00073 deltaE 89.6
    ---                                                   M00001 MyoD   88.4
                                              ----------- M00075 GATA-1 87.8
                                               <--------- M00096 Pbx-1  86.3
    ->                                                    M00220 SREBP- 85.9
                                              ----------- M00209 NF-Y   85.9
    ---->                                                 M00122 USF    85.3
    ----                                                  M00122 USF    85.3

501 TCCGCCCGGC ACCGGGAAGA GCCGTTATGC ATTTGAATTT CCCGCCGAAA entry     score
                          <----------                     M00227 v-Myb  93.6
                                                       -- M00148 SRY    90.9
                                         --------->       M00050 E2F    90.8
    >                                                     M00075 GATA-1 87.8
                                <------------------       M00133 Tst-1  87.5
    -                                                     M00096 Pbx-1  86.3
    ---->                                                 M00209 NF-Y   85.9
                       <-----------                       M00003 v-Myb  85.9

551 ACAAGTATTA CA                                                entry   score
    ---->                                                 M00148 SRY    90.9
```

Fig. 17 (f)

7. Finch circovirus

```
                  CCGTGAAAGC CGGAAGAGGT ATGGCCGAAG TCGCGGGAGA entry        score
                     ----------->                           M00108 NRF-2  93.0
                     ----------->                           M00032 c-Ets- 88.2
                                               <---------   M00050 E2F    86.2

401 GTTCAGTCTA GCCTACGTCA GATATGGGCG GGGCCTGCGT GATCTTGCGC entry        score
                  <---------                                M00039 CREB   91.6
                     --------------->                       M00128 GATA-1 91.5
                       ----------->                         M00077 GATA-3 89.1
                              ------------>                 M00008 Sp1    89.0
                      ------------>                         M00076 GATA-2 88.9
                                           ------------>    M00075 GATA-1 87.3

451 TGCTGATTGG CCAGAAGCCC CGTGACTTCA AAACGGAAGT CATAGTGCTG entry        score
      ------------>                                         M00075 GATA-1 91.8
                                ----------------->          M00074 c-Ets- 90.5
                               ------------------>          M00025 Elk-1  90.0
      ---------------->                                     M00209 NF-Y   89.4
                                  ------------->            M00108 NRF-2  87.7
                         --------->                         M00041 CRE-BP 87.2
                     ---------->                            M00217 USF    86.6
                                  ------------>             M00032 c-Ets- 86.3
                         <---------                         M00041 CRE-BP 86.2
                         --------->                         M00039 CREB   86.1
                              ------------>                 M00003 v-Myb  85.9
                         <---------                         M00039 CREB   85.6

501 ACCGGCCCTA GTGGGTGTGG CAAATCCCGC TGGGCCAATG AACAAGAAGG entry        score
                     <------------                          M00054 NF-kap 88.8
                    <-------------                          M00208 NF-kap 86.2
                      <------------                         M00053 c-Rel  85.1

551 AACTAAGTTT T                                            entry        score
```

Fig. 17 (g)

8. Goose circovirus

```
                      TGGTCTGCCG ATAACTGACG TGGCCCGGAA entry        score
                                           ---------   M00032 c-Ets- 95.1
                                       ------------    M00025 Elk-1  93.0
                        ------------>                  M00076 GATA-2 89.3
                                        -----------    M00074 c-Ets- 87.7
                                              <-----   M00053 c-Rel  86.8
                      ----------------->               M00127 GATA-1 86.7
                        ------------>                  M00075 GATA-1 86.5
                                  ---------->          M00039 CREB   86.1

401 GTACCCGACG ACTTATGTAA TGTTTGGGCG GGGCTTAGAG CGGTTGCGTC entry        score
     --->                                              M00032 c-Ets- 95.1
               --------------->                        M00045 E4BP4  93.1
     ---->                                             M00025 Elk-1  93.0
            ------------------->                       M00109 C/EBPb 90.6
                <------------                          M00228 VBP    89.8
                          ------------->               M00008 Sp1    89.0
```

Fig. 17 (h)

```
                        <-------                                     M00040 CRE-BP  89.0
     ---->                                                           M00074 c-Ets-  87.7
                                   ---------->                       M00141 Lyf-1   87.0
     ------                                                          M00053 c-Rel   86.8
                        ------->                                     M00040 CRE-BP  86.7
                    <----------------                                M00116 C/EBPa  86.5
                      ------->                                       M00101 CdxA    86.4
                                      <------------                  M00072 CP2     85.4
                                                           <-------  M00039 CREB    85.1

451 AGCTGATCGT GGAGACCGCT CGTGATTGGA AGACGGAGGT CATCGTTCTG entry          score
                                 ---------->                         M00075 GATA-1  92.2
      ----------->                                                   M00075 GATA-1  91.4
                                                              ----   M00075 GATA-1  89.4
                                                               ---   M00077 GATA-3  87.5
      ----------->                                                   M00076 GATA-2  85.8
    -                                                                M00039 CREB    85.1

501 ATTGGGCGGC CTGGAAGCGG GAAGAGCCGT TACGCGTTTG AATTTCCCGC entry          score
                                    <----------                      M00227 v-Myb   96.3
                                                         -------->   M00050 E2F     90.8
    ------>                                                          M00075 GATA-1  89.4
    ----->                                                           M00077 GATA-3  87.5

551 GCGTGAAAAG TATTATAAAT                                      entry    score
                   <------                                   M00101 CdxA    100.0
                   <------                                   M00100 CdxA     96.2
                ------->                                     M00101 CdxA     91.4
                <-------                                     M00101 CdxA     91.4
    <--------                                                M00050 E2F      88.5
```

Fig. 17 (h) (Continued)

9. Gull circovirus

```
                              GTGAAATCGC GCGAGAGTTC AGTGAAGTCT entry          score
                                                           <-  M00039 CREB    91.6
                                   <---------                  M00050 E2F     86.2

451 ACGTCAAGTA TGGGCGGGGC CTCCGTGATC TCCGGTTGCT GATTGGTTGC entry          score
                                                ----------->   M00075 GATA-1  93.5
    ------                                                     M00039 CREB    91.6
                                                -------------  M00209 NF-Y    90.6
              ---------->                                      M00008 Sp1     89.0
                                                           <-- M00008 Sp1     89.0
      ------->                                                 M00240 Nkx-2.  88.4
                                            <----------        M00096 Pbx-1   86.3
                                 <--------------               M00074 c-Ets-  86.2
                                  <----------                  M00032 c-Ets-  85.3

501 CCGCCCCGCG ATTTCAAAAC AGAAGTCATC GTTCTGATTG GCCCACCTGG entry          score
    >                                                          M00209 NF-Y    90.6
                     -------->                                 M00148 SRY     90.0
               <-----------------                              M00109 C/EBPb  89.3
    -------                                                    M00008 Sp1     89.0
                                                  -----------  M00073 deltaE  86.2
                                      ----------->             M00075 GATA-1  86.1

551 CTGTGGCAAG TCAAAATTGG CCAATGAGAT GGAAGGGTCT AAGTTCTACA entry          score
```

Fig. 17 (i)

```
                                                  --- M00011 Evi-1   89.1
                                   ---------->        M00147 HSF2    87.2
     >                                                M00073 deltaE  86.2
                   --------------->                   M00116 C/EBPa  85.3
```

Fig. 17 (i) (Continued)

PCV-1 Pcap region

```
        GCAGTTCCCT GTAACGTATG TGAGAAATTT CCGCGGGCTG entry         score
                              <-----------          M00147 HSF2    91.0
                              ----------->          M00147 HSF2    88.5
                              ----------->          M00146 HSF1    87.3
                                <-------------      M00074 c-Ets-  86.6

451 GCTGAACTTT TGAAAGTGAG CGGGAAGATG CAGCAGCGTG ATTGGAAGAC entry         score
                                     ----------->    M00075 GATA-1  92.2
      --------------->                               M00109 C/EBPb  85.5

501 AGCTGTACAC GTCATAGTGG GCCCGCCCGG TTGTGGGAAG AGCCAGTGGG entry         score
                              <---------             M00223 STATx   88.5
        <---------                                   M00039 CREB    87.6

            551 CCCGTAATTT TGCTGAGCCT AGCGACACCT ACTGGAAGCC entry         score
                                  ---------->        M00032 c-Ets-  89.2
     <-------                                        M00101 CdxA    85.7
```

Fig. 17 (j)

PCV-2 Pcap region

```
       CAGA GCAGCACCCT GTAACGTTTG TCAGAAATTT CCGCGGGCTG entry         score
                              <-------               M00101 CdxA     93.6
                               <-----------          M00147 HSF2     91.0
                              <-------               M00100 CdxA     89.7
                               ----------->          M00147 HSF2     88.5
                               ----------->          M00146 HSF1     87.3
                                  <-------------     M00074 c-Ets-   86.6

451 GCTGAACTTT TGAAAGTGAG CGGGAAAATG CAGAAGCGTG ATTGGAAGAC entry         score
                                     ----------->    M00075 GATA-1   92.2
                     <---------                      M00050 E2F      90.8
                                                  -- M00101 CdxA     86.4
      --------------->                               M00109 C/EBPb   85.5

501 TAATGTACAC GTCATTGTGG GGCCACCTGG GTGTGGTAAA AGCAAATGGG entry         score
                               ------>               M00271 AML-1a  100.0
     <------------------                             M00251 XBP-1    88.0
                            ---------------->        M00159 C/EBP    87.7
          <---------                                 M00039 CREB     87.6
   ---->                                             M00101 CdxA     86.4
                                         -------->   M00148 SRY      86.4
        <----------------                            M00162 Oct-1    85.7

551 CTGCTAATTT TGCAGACCCG GAAACCACAT ACTGGAAACC            entry         score
```

Fig. 17 (k)

```
           <------                              M00271 AML-1a 100.0
   -------------->                              M00032 c-Ets- 86.3
```

Fig. 17 (k) (Continued)

EXPRESSION SYSTEM INCORPORATING A CAPSID PROMOTER SEQUENCE AS AN ENHANCER

CROSS REFERENCE TO RELATED APPLICATIONS

This application is the U.S. National Phase of PCT/IB2006/003150 filed on 8 Nov. 2006 which claims priority to South African Patent Application No. 2005/09036 filed on 8 Nov. 2005, the contents of which are incorporated by reference herein.

BACKGROUND OF THE INVENTION

The invention describes a new mammalian composite promoter/enhancer expression element.

The cytomegalovirus immediate/early enhancer/promoter element (Pcmv) is currently the strongest known mammalian promoter element, and as such puts an upper limit on transgene expression in in vitro and in vivo systems.

It would therefore be desirable to be able to include a further element in a vector that allows increased transgene expression to be attained.

SUMMARY OF THE INVENTION

According to a first embodiment of the invention, there is provided a method for enhancing expression of a transgene in a host cell, the method including the steps of:

- inserting a sequence of a capsid promoter (Pcap) element or a reverse complement thereof (PcapR) into a mammalian expression cassette upstream (5') of a cytomegalovirus immediate/early promoter (Pcmv);
- inserting the transgene into the expression cassette downstream (3') of the cytomegalovirus promoter;
- inserting the expression cassette into the host organism; and
- causing expression of the transgene.

A cytomegalovirus intron may be inserted downstream (3') of the Pcmv and a bovine growth hormone polyadenylation site (bgh polyA) may be inserted downstream (3') of the transgene.

The transgene is typically expressed at a higher level than when expressed in the expression cassette without the Pcap or PcapR sequence.

The capsid promoter element or reverse complement thereof may be from a circovirus such as porcine circovirus type 1 (PCV-1), porcine circovirus type 2 (PCV-2), beak and feather disease virus (BFDV), canary circovirus, columbid circovirus, duck circovirus, finch circovirus, goose circovirus and gull circovirus or a corresponding element from a parvovirus or an anellovirus.

The capsid promoter element or reverse complement thereof may be located adjacent to the cytomegalovirus immediate/early promoter, or alternatively may be located up to 1100 base pairs upstream (5') of the cytomegalovirus immediate/early promoter.

The host cell may be a mammalian cell line for in vitro transgene expression. Alternatively, the host cell may be a cell of a mammalian host organism for in vivo transgene expression.

According to a second embodiment of the invention, there is provided a mammalian expression cassette including:

- a cytomegalovirus immediate/early promoter (Pcmv); and

- a capsid promoter element sequence (Pcap) or a reverse complement (PcapR) thereof located upstream (5') of the cytomegalovirus promoter.

A transgene may be inserted into the expression cassette downstream (3') of the CMV promoter.

The expression cassette may be capable of expressing the transgene at a higher level than a similar expression cassette which does not include the Pcap or PcapR sequence.

The capsid promoter element or reverse complement thereof may be from a circovirus such as porcine circovirus type 1 (PCV-1), porcine circovirus type 2 (PCV-2), beak and feather disease virus (BFDV), canary circovirus, columbid circovirus, duck circovirus, finch circovirus, goose circovirus and gull circovirus or a corresponding element from a parvovirus such as canine parvovirus, or an anellovirus such as torque teno virus and torque teno mini virus.

The Pcap or PcapR sequence may be at least 80% identical, more preferably at least 90% identical, and even more preferably at least 95%, and even more preferably 100% identical to any one of SEQ ID NOs: 1 to 18, 21, 22 or 24.

According to a further aspect of the invention, there is provided a vector which includes the expression cassette as described above.

The expression cassette or vector may be inserted into a host cell, which may be a mammalian cell line for in vitro transgene expression or a cell of a mammalian host organism for in vivo transgene expression.

According to a further aspect of the invention there is provided a host cell transformed with the expression cassette or vector as described above.

According to a further embodiment of the invention, there is provided a DNA vaccine including an expression cassette or vector as described above.

According to a further embodiment of the invention, there is provided a pharmaceutical composition including the expression cassette or vector as described above.

According to a further embodiment of the invention, there is provided the use of a DNA vector as described above in a method of making a medicament for use in a method of treating a disease.

According to a further embodiment of the invention, there is provided a method of treating a patient, the method including the step of administering a DNA vaccine as described above to the patient.

The pharmaceutical composition or DNA vaccine may be used for therapeutic or prophylactic treatment of a disease or infection, such as HIV and/or AIDS.

- (a) Depiction of native circular porcine circovirus type 1 (PCV-1) genome; PCV-1 genome linearised within the capsid gene, with addition of terminal Spe I restriction sites; pTHRep(R)grttnC wherein the linearised pCV-1 genome is cloned immediately 5' to Pcmv (CMV I/E Pr);
- (b) Linear depiction of relevant regions of pTHRepRgrttnC, pTHPcapgrttnC and pTHPcapRgrttnC plasmids, illustrating the relative positions and orientations of the cloned 184 bp Pcap-containing sequence in relation to Pcmv and grttnc.

FIG. 2: Demonstration that PCV-1-containing vectors do not replicate in mammalian cells: Real-time PCR quantitation of intact and DpnI-digested plasmid extracted from 293 cells 1-3 days post transfection:

(a) 293 cells transfected with pTHgrttnC, pTHRepgrttnC, or pTHRepRgrttnC, with or without addition of plasmid pcDNARep (expresses PCV-1 Rep and Rep' proteins under Pcmv, and potentially trans-replicates circular DNAs containing the PCV-1 origin of replication, as per pTHRepgrttnC and pTHRepRgrttnC). DNA extracted from transfected cells at 48 h after transfection. Results demonstrate that the PCV-1 containing plasmids neither replicate nor can be trans-replicated from pcDNARep.

(b) 293 cells transfected with pCI and pCIPCV (original plasmids received from LSBC, and presumed to be replicating). Results demonstrate that like the non-replicating parental plasmid, pCI, the PCV-1-containing plasmid, pCIPCV, does not replicate in 293 cells.

FIG. 3: Demonstration that Prep enhances expression from Pcmv, and that no plasmid replication is involved:

Deletion of the rep gene intron enhances expression over pTHgrttnC, despite loss of the ability to make the full-length Rep protein to repress Prep. Deletion of the Rep/Rep' binding site in Prep and most of the rep gene in pTH□RepgrttnC still allows some enhancement of expression over pTHgrttnC, since the residual Prep still encodes all of the host transcription factor binding sites in Prep.

Figure 4:
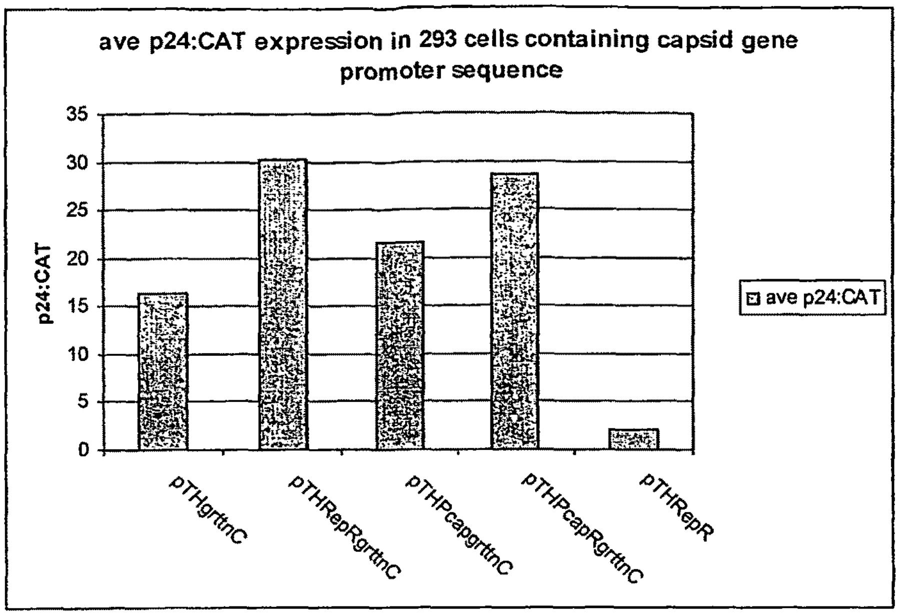

FIG. 4: Demonstration that incorporation of either the Pcap sequence or the PcapR sequence alone into pTHgrttnC gives similar p24 antigen expression levels to incorporation of the entire PCV-1 genome in pTHgrttnC (ie pTHRepRgrttnC). Addition of the 184 bp fragment (PcapR) in the opposite orientation alone into pTHgrttnC (to give pTHPcapRgrttnC) enhances expression to a similar extent.

Figure 5:
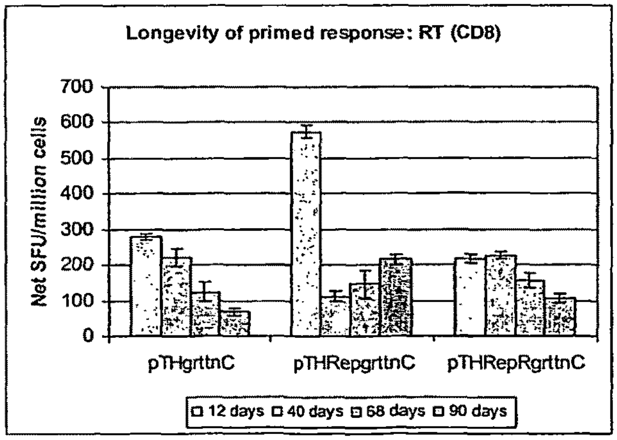

FIG. 5: Longevity of primed CTL response to RT CD8 epitope of grttnc over 90 days by PCV-1 sequence-containing vectors.

Female BALB/c mice (5 animals per group) were inoculated intramuscularly with 2×100 μg doses, given 28 days apart, of pTHgrttnC, pTHRepgrttnC, pTHRepRgrttnC, or empty pTHRepR vector (not shown). Mice were sacrificed at 12, 40, 68, and 90 days after the second DNA inoculation, and splenocytes harvested for IFN-γ ELISPOT assay. Average background spots were subtracted to give net spots/$10^6$ splenocytes.

Figure 6:
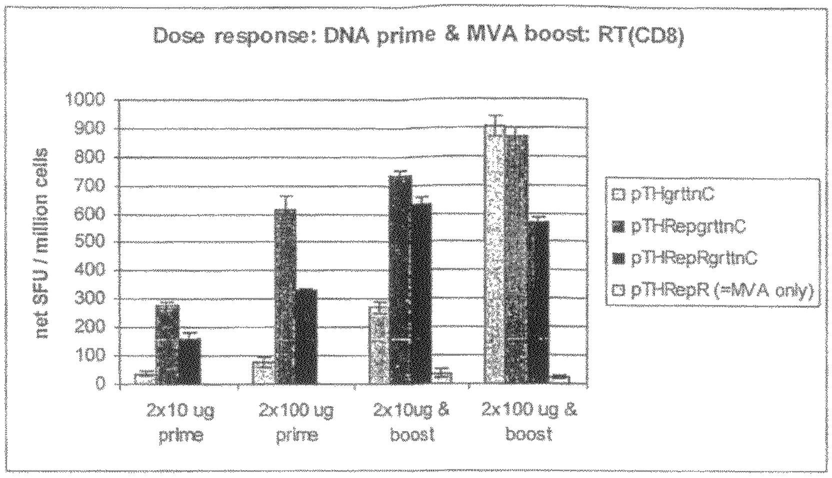

FIG. 6: CTL response to RT CD8 epitope of grttnC. DNA priming dose response with and without an MVA boost.

Female BALB/c mice (5 animals per group) were inoculated intramuscularly with 2×100 ug or 2×10 ug doses, given 28 days apart, of pTHgrttnC, pTHRepgrttnC, pTHRepRgrttnC, or empty pTHRepR vector (not shown). Mice were sacrificed at 12 days after the second DNA inoculation, and splenocytes harvested for IFN-γ ELISPOT assay. Further groups of mice, inoculated as above, were boosted with 10e4 pfu SAAVIMVA-C (r.grttnc cloned into MVA) 56 days after the second DNA boost. Mice were sacrificed at 12 days after the MVA boost, and splenocytes harvested for IFN-γ ELISPOT assay. Average background spots were subtracted to give net spots/$10^6$ splenocytes.

Figure 7:
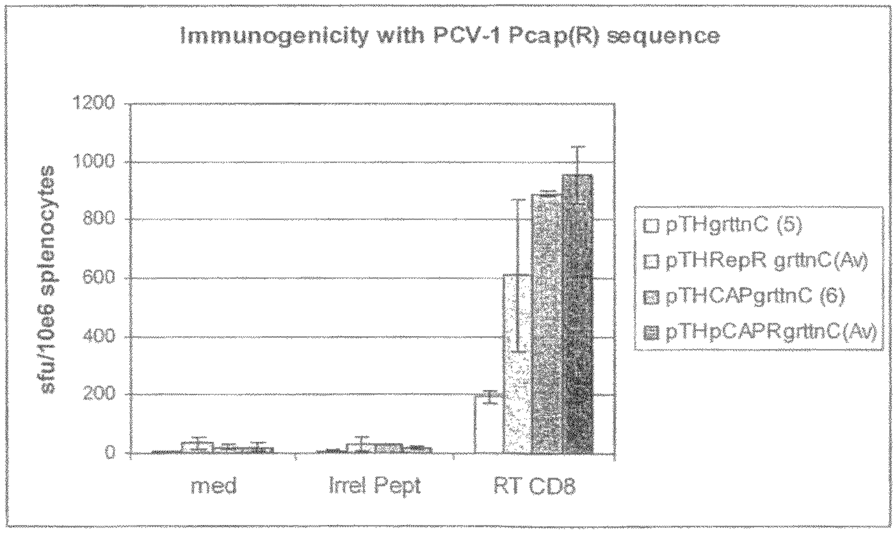

FIG. 7: CTL response to RT CD8 epitope of grttnc. Comparisons between pTHgrttnC, pTHRepRgrttnC, pTHPcapgrttnC and pTHPcapRgrttnC as DNA priming dose.

Female BALB/c mice (5 animals per group) were inoculated intramuscularly with 2×100 ug doses, given 28 days apart, of pTHgrttnC, pTHRepRgrttnC, pTHPcapgrttnC, or pTHPcapRgrttnC. Mice were sacrificed at 12 days after the second DNA inoculation, and splenocytes harvested for IFN-γ ELISPOT assay. Average background spots were subtracted to give net spots/$10^6$ splenocytes.

FIG. 8: Nucleotide sequence of Pcap fragment showing host cell transcription factor binding sites.

190 bp shown (SEQ ID NO: 27) however, upon cloning into Spe I site in vector, essentially, fragment can be considered to be 184 bp (SEQ ID NO: 1). The Pcap sequence is shown in the same orientation as the capsid gene transcription direction. Note that as a result the sequence shown below is the reverse complement of the publishing convention that depicts circovirus DNA sequence in the (+) virion sense.

The core Pcap region (102 bp) as identified in Mankertz et al., 2004, is shown underlined.

Cloning Spe I sites are shown in italics (ACTAGT)

Nucleotide 44=A shown in bold=nucleotide difference (sense strand C to T transition) with respect to published PCV-1 sequences.

As reported in Mankertz et al., 2004,

Highlighted sequence nucleotides 47-59=motif for host cell AP3 transcription factor binding Highlighted sequence nucleotides 60-65=motif for host cell Sp1 transcription factor binding Highlighted sequence nucleotides 139-144=motif for host cell AP2 transcription factor binding As identified using the on-line database search engine, TFSEARCH ver. 1.3;

Bold sequence nucleotides 28-34=motif for host cell cdxA transcription factor binding Bold sequence nucleotides 48-56=motif for host cell STATx transcription factor binding Bold sequence nucleotides 73-80=motif for host cell CREB transcription factor binding Bold sequence nucleotides 140-152=motif for host cell c-Ets-transcription factor binding Bold sequence nucleotides 145-154=motif for host cell HSF2 transcription factor binding FIG. 9: Nucleotide sequence of PcapR fragment showing host cell transcription factor binding sites.

190 bp shown (SEQ ID NO: 28) however, upon cloning into Spe I site in vector, essentially, fragment can be considered to be 184 bp (SEQ ID NO: 2). The PcapR sequence is shown in the opposite orientation to the capsid gene transcription direction. Note that as a result, the sequence shown below depicts the circovirus (+) virion sense DNA sequence.

Cloning Spe I sites are shown in italics (ACTAGT)

Nucleotide 147=T shown in bold=nucleotide difference (sense strand C to T transition) with respect to published PCV-1 sequences.

As identified using the on-line database search engine, TFSEARCH ver. 1.3;

Bold sequence nucleotides 37-46=motif for host cell HSF1/HSF2 transcription factor binding Bold sequence nucleotides 59-72=motif for host cell c/EBPb transcription factor binding Bold sequence nucleotides 91-100=motif for host cell GATA-1 transcription factor binding Bold sequence nucleotides 125-130=motif for host cell AP2 transcription factor binding Bold sequence nucleotides 145-154=motif for host cell HSF2 transcription factor binding Highlighted nucleotides 120-129 and 149-158=conserved late element (CLE), as identified in Velten et al., 2005.

FIG. 10: grttnC DNA sequence (SEQ ID NO: 19).

Hind III site (bold, highlighted nucleotides 1-6) and Xba I site (bold, highlighted nucleotides 3682-3687)=sites for cloning grttnC sequence into pTH.

FIG. 11: Linearised PCV-1 DNA sequence, as cloned into pTHgrttnC to give pTHRepgrttnC (SEQ ID NOs: 21 and 29).

Terminal Spe I sites (bold) used to clone linearised PCV-1 genome into Spe I restriction site immediately 5' adjacent to CMV promoter in pTHgrttnC.

FIG. 12: Linearised PCV-1 DNA sequence, as cloned (reverse complement) into pTHgrttnC to give pTHRepRgrttnC (SEQ ID NOs: 22 and 30).

Terminal Spe I sites (bold) used to clone linearised PCV-1 genome into Spe I restriction site immediately 5' adjacent to CMV promoter in pTHgrttnC.

FIG. 13: Linearised sequence of pTH (SEQ ID NO: 20).

Showing Spe I site (bold, underlined, highlighted nucleotides 751-756) immediately 5' to core region of CMV immediate/early promoter/enhancer element of pTH. This is the insertion site used for linearised PCV-1 genome (either orientation), and Pcap, and PcapR.

Hind III site (bold, highlighted nucleotides 2300-2315) and Xba I site (bold, highlighted nucleotides 2394-2399)=cloning sites for grttnC insert.

FIG. 14: PCV-1 sequence showing Prep and intron-deleted rep gene (encodes Rep' protein only) (SEQ ID NO: 23).

As reported in Mankertz et al., 2004.

Highlighted sequence nucleotides 69-80=motif for host cell AP3 transcription factor binding Highlighted sequence nucleotides 120-125=motif for host cell Sp1 transcription factor binding Highlighted sequence nucleotides 187-192=motif for host cell AP4 transcription factor binding Highlighted sequence nucleotides 153-164=host cell USF/MLTF motif Highlighted sequence nucleotides 166-172=TATA box Highlighted sequence nucleotides 174-180=ISRE motif H1, H2, H3 and H4 Rep/Rep' binding motifs are shown underlined.

ATG and TGA of (truncated) rep' open reading frame are shown in bold.

FIG. 15: PCV-1 sequence showing Prep with deletion of Rep/Rep' protein binding sites and severely 5' truncated rep gene (non-coding remnant) (SEQ ID NO: 24).

PCV-1 sequence showing 602 bp deletion, leading to inclusive deletion of the H2, H3 and H4 Rep/Rep' binding sites in Prep and deletion of all but 133 of the 3'-terminal nucleotides of the rep gene.

II=site of 602 bp deletion

As reported in Mankertz et al., 2004.

Highlighted sequence nucleotides 69-80=motif for host cell AP3 transcription factor binding Highlighted sequence nucleotides 120-125=motif for host cell Sp1 transcription factor binding Highlighted sequence nucleotides 187-192=motif for host cell AP4 transcription factor binding Highlighted sequence nucleotides 153-164=host cell USF/MLTF motif Highlighted sequence nucleotides 166-172=TATA box Highlighted sequence nucleotides 174-180=ISRE motif H1 residual Rep/Rep' binding motif is shown underlined.

FIG. 16: (a) Alignment of selected circovirus DNA sequences equivalent to PCV-1 PcapR region.

(b) Selected circovirus reverse complement DNA sequences equivalent to PCV-1 Pcap sequence.

Canary circovirus: ACCESSION DQ339095 (SEQ ID NOs: 3 and 4);

Goose circovirus: ACCESSION NC.sub. 003054 (SEQ ID NOs: 5 and 6);

Duck circovirus: ACCESSION AJ964962 (SEQ ID NOs: 7 and 8);

Columbid circovirus isolate zjl: ACCESSION DQ090945 (SEQ ID NOs: 9 and 10);

Gull circovirus: ACCESSION NC.sub. 008521 (SEQ ID NOs: 11 and 12);

Finch circovirus: ACCESSION NC.sub. 008522 (SEQ ID NOs: 13 and 14);

Beak and feather disease virus isolate AFG3-ZA: ACCESSION AY450443 (SEQ ID NOs: 15 and 16);

Porcine circovirus type 2 strain 375: ACCESSION AY256460 (SEQ ID NOs: 17 and 18).

Figure 17K:
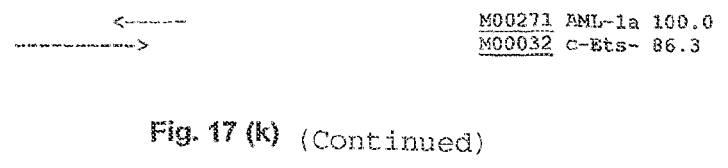

FIG. 17: Potential transcription factor binding sites in the Pcap regions of the circoviruses of FIG. 16. FIG. 17(*a*) shows nucleotides at positions 1080-1259 of SEQ ID NO:21. FIG. 17(*b*) shows nucleotides at positions 7-190 of SEQ ID NO:17. FIG. 17(*c*) shows nucleotides at positions 5-170 of SEQ ID NO:15. FIG. 17(*d*) shows nucleotides at positions 11-170 of SEQ ID NO:3. FIG. 17(*e*) shows nucleotides at positions 1-174 of SEQ ID NO:9. FIG. 17(*f*) shows nucleotides at positions 1-182 of SEQ ID NO:7. FIG. 17(*g*) shows SEQ ID NO:31. FIG. 17(*h*) shows SEQ ID NO:32. FIG. 17(*i*) shows nucleotides at positions 1-180 of SEQ ID NO:11. FIG. 17(*j*) shows nucleotides at positions 1080-1259 of SEQ ID NO:21. FIG. 17(*k*) shows nucleotides at positions 7-190 of SEQ ID NO:17.

DETAILED DESCRIPTION OF THE INVENTION

The invention provides a method for enhancing expression of a transgene in a host cell, which includes the steps of inserting a viral transcriptional control element into a mammalian expression cassette upstream (5') of a main promoter for a vector, inserting the transgene into the expression cassette downstream (3') of the main promoter, inserting a vector containing the expression cassette into the host organism; and causing expression of the transgene. As a result, the transgene is typically expressed at a higher level than when expressed by a vector containing the expression cassette without the transcriptional control element.

The transcriptional control element is a capsid promoter element (Pcap) of a circovirus, such as porcine circovirus type 1 (PCV-1), porcine circovirus type 2 (PCV-2), beak and feather disease virus (BFDV), canary circovirus, columbid circovirus, duck circovirus, finch circovirus, goose circovirus and gull circovirus or a corresponding element from a parvovirus or anellovirus, or a sequence comprising the reverse complement of the capsid promoter element (PcapR). The promoter is generally a cytomegalovirus immediate/early enhancer/promoter region (Pcmv) and optionally its downstream (3') CMV intron A sequence, a SV40 promoter element, or another suitable promoter element.

Examples of suitable host cells are a mammalian cell line for in vitro transgene expression or a mammalian host organism for in vivo transgene expression.

The vector as described herein has various uses, including the production of a pharmaceutical composition or vaccine for prophylactically or therapeutically treating a human or animal with an infection or disease, such as HIV/AIDS.

In the examples below, a 184 bp DNA fragment (FIG. 8; SEQ ID NO: 1) containing a 102 bp main capsid promoter element (Pcap) of porcine circovirus type 1 (PCV-1), or the same 184 bp fragment cloned in the reverse orientation (PcapR) (FIG. 9; SEQ ID NO: 2), was inserted immediately adjacent and 5' to the core region of the cytomegalovirus immediate/early enhancer/promoter region (Pcmv) and its downstream (3') CMV intron A sequence in a mammalian expression vector (the fragment was 190 bp when flanked by uncut restriction sites (SEQ ID NO: 27)). A transgene was subsequently cloned into the vector. Purified plasmid containing the above elements was either transfected into a mammalian cell line for in vitro transgene expression, or was inoculated into a mammalian host organism as a vaccinogen or gene therapy agent. The Pcap-Pcmv hybrid or the PcapR-Pcmv hybrid led to a 2- to 3-fold enhanced expression in vitro of a transgene inserted 3' to the Pcap-Pcmv hybrid element or 3' to the PcapR-Pcmv hybrid element.

Figure 1:
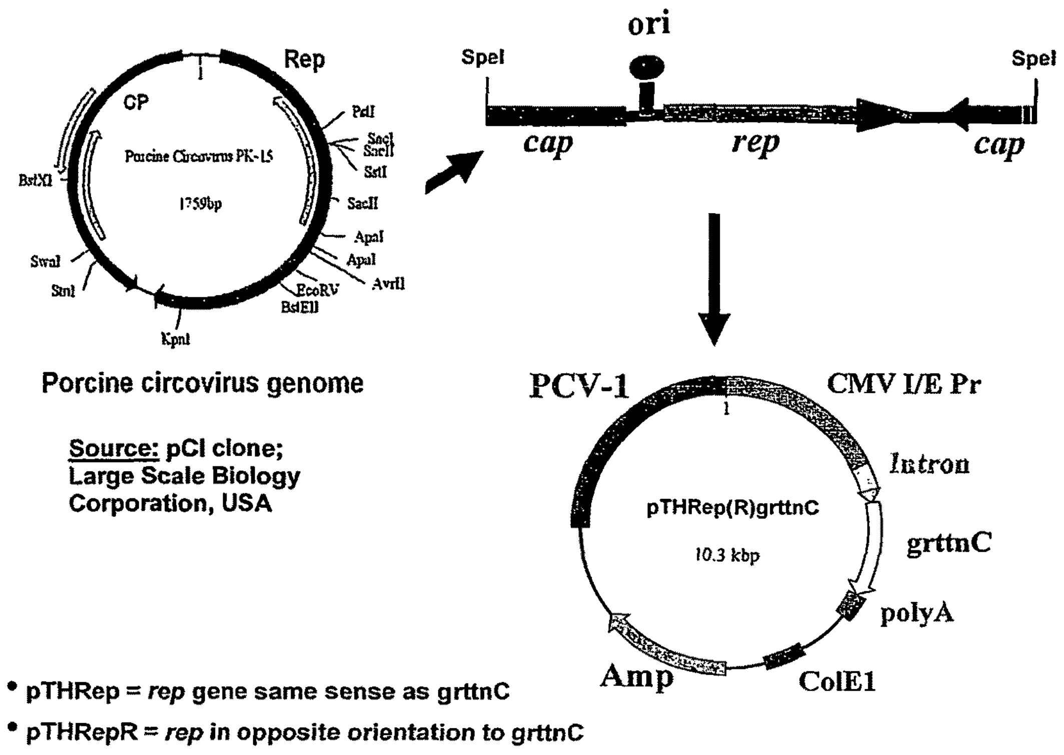
FIG. 1: Cloning of initial PCV-1-containing vector constructs and of Pcap- and PcapR-containing constructs.
Figure 1:
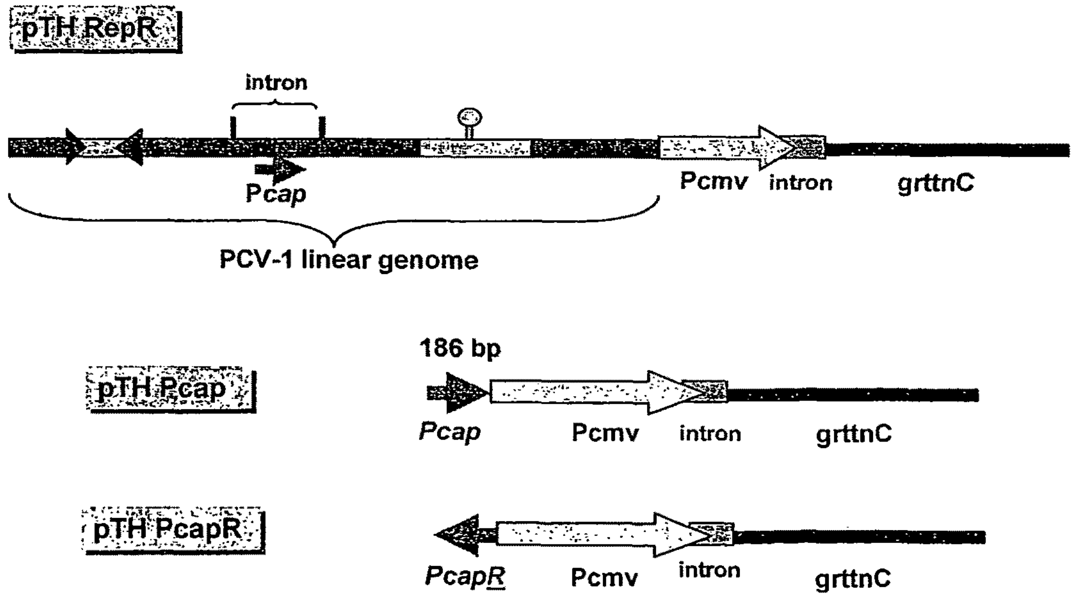

The PCV-1 Pcap promoter element referred to above has previously been mapped utilising a luciferase expression system (Mankertz et al.), but until now it has not been envisaged as being of utility in practical applications of transgene expression, since by itself it is not a strong promoter. In addition, the full 184 bp fragment includes further host transcription factor binding sites not previously noted by Mankertz et al. It has also not been previously envisaged that the reverse oriented sequence (PcapR) also confers transgene expression enhancing activity, and that further host transcription factor binding sites are encoded in the PcapR sequence. The Pcmv element has previously been combined with different downstream (3') intron donor/acceptor elements, which increase transgene expression levels by improving transgene mRNA transcript processing efficiency (Barouch et al., 2005). The pTH vector is a high level expression vector, and contains a resident intron sequence downstream of the CMV promoter (FIG. 1A). However, the addition of a Pcap element or a PcapR element into the plasmid pTHgrttnC upstream of the CMV promoter in pTH (FIG. 1B) gives rise to a further increase in grttnc expression levels over and above the existing contribution of the resident intron sequence in pTHgrttnC.

It is envisaged that the Pcap or PcapR elements may retain enhancing activity when cloned up to 1100 bp upstream (5') of the Pcmv element (this is the distance of the Pcap element from Pcmv when Pcap is present in the parent RepR sequence in pTHRepRgrttnC). It is also envisaged that the invention will work with corresponding Pcap or PcapR elements from other circoviruses (FIGS. 16 and 17), such as porcine circovirus type 2 (PCV-2) (SEQ ID NOs: 3 and 4), Beak and Feather Disease Virus (BFDV) (SEQ ID NOs: 5 and 6), canary circovirus (SEQ ID NOs: 7 and 8), columbid circovirus (SEQ ID NOs: 9 and 10), duck circovirus (SEQ ID NOs: 11 and 12), finch circovirus (SEQ ID NOs: 13 and 14), goose circovirus (SEQ ID NOs: 15 and 16) and gull circovirus (SEQ ID NOs: 17 and 18) or parvoviruses such as canine parvovirus, or anelloviruses, such as torque teno virus and torque teno mini virus, since these virus genera belong to the same family as the circoviruses.

The present invention is further described by the following examples. Such examples, however, are not to be construed as limiting in any way either the spirit or scope of the invention.

EXAMPLES

PCV Cloning and Expression

To facilitate comparisons with the applicants' existing DNA vaccine construct, pTHgrttnC (Burgers et al; FIGS. 10 & 13; SEQ ID NOs: 19 and 20), a linearised PCV-1 genome (FIG. 11 SEQ ID NOs: 21 and 29) derived from plasmid pCIPCV 9 (obtained from Large Scale Biology Corporation; USA; and described in US patent application publication no. 2003/0143741, the contents of which are incorporated herein in their entirety), was sub-cloned into pTHgrttnC so that the genome was positioned immediately 5' to the CMV immediate/early promoter/enhancer (Pcmv) in pTHgrttnC. The PCV genome was cloned in both orientations (FIG. 1), giving pTHRepgrttnC, where the PCV replication-associated gene (rep) lies in the same orientation as the gttrnC polygene insert (FIG. 11; SEQ ID NOs: 21 and 29), and pTHRepRgrttnC, where rep lies in the opposite orientation to grttnc (FIG. 12; SEQ ID NOs: 22 and 30).

Increased antigen expression levels were shown by both pTHRepgrttnC and pTHRepRgrttnC in HEK293 cells compared to pTHgrttnC, with pTHRepRgrttnC showing the highest expression. Expression of grttnc was assayed by p24 ELISA and correlated with amount of plasmid present in cell samples (assayed by real-time PCR).

It was noted that orientation of the inserted PCV genome in pTHgrttnC affected both the level and pattern of grttnc expression obtained over time, and this was investigated further.

Increased Expression in PCV Vector Due to Promoter Effects and not Due to Vector Replication:

HEK293 cells (from American Type Culture Collection (ATCC catalogue number CRC1573)) were transfected with plasmid DNA, and harvested at 1, 2, and 3 days post-transfection. After cell washing, total DNA was extracted and plasmid present in 20 ng of the extract was quantified by real-time PCR, using Sybr green incorporation and vector-specific oligonucleotide primers. The primer sequences used bind to plasmids pTH (pTHgrttnC), pCI (Promega) and pcDNA3.1/Zeo (Invitrogen)-pTH17F; 5'-CCTAACTACGGCTACAC-3' (SEQ ID NO: 25); pTH18R; 5'-CGTAGTTATCTACACGAC-3' (SEQ ID NO: 26). The primer sequences were obtained from Jo van Harmelen, IIDMM, South Africa. Additionally, total DNA aliquots were digested overnight with the restriction enzyme, Dpn I (from Roche), which, due to its methylation specificities, digests only bacterially produced transfected plasmid DNA (input DNA), but not any DNA that may have been replicated in mammalian cells (eg HEK293). The digested plasmid (in total DNA) was also quantified by PCR as before. Equivalent amounts of digested and undigested total DNAs were used. (Replicating refers here to the ability of the plasmid to replicate in mammalian cells, rather than in bacterial cells).

Improved expression of the PCV vectors over pTH (FIG. 13; SEQ ID NO: 20) was found and was demonstrated to be due to PCV promoters acting in concert with Pcmv in pTH, and not due to vector replication (FIG. 2, FIG. 3). Thus, in pTHRepgrttnC, the rep gene promoter (Prep) acts in concert with Pcmv, and in pTHRepRgrttnC, the PCV capsid gene promoter (Pcap) acts with Pcmv.

Experiments to demonstrate this included:

- Demonstration (using Dpn I digestion/real-time pcr) that no plasmid replication occurred in transfected cells. Thus, the proportion of plasmid extracted from transfected cells declined over time at the same rate as the non-PCV-containing parent plasmid and no new plasmid was formed in transfected cells during that time. This was determined for both the applicants' and Large Scale Biology Corporation's PCV-based constructs (FIG. 2).
- Deletion of the PCV-1 rep intron (FIG. 14; SEQ ID NO: 23) from pTHRepgrttnC resulted in increased grttnc expression (FIG. 3). This deletion prevents the formation of one of the Rep proteins required for replication. The same protein acts to repress Prep, and its absence allows for relief from Prep repression, with resulting increased accumulation of expressed GrttnC. Thus, increased expression in pTHRep GrttnC results from activity of Prep rather than from replicative increase in plasmid copy number. Deletion of the Rep/Rep' protein binding sites in Prep and deletion of most of the rep gene from the 5' end, but still leaving host transcription factor binding sites in Prep (FIG. 15; SEQ ID NO: 24), yields a modest increase in expression over pTH, further indicating the action of promoter elements, rather than PCV-1 element-driven plasmid replication as the source of increased transgene expression in PCV-1 sequence-containing plasmids (FIG. 3).

Addition of the 184 bp Pcap-containing sequence alone (SEQ ID NO: 1) into pTHgrttnC improved grttnc expression to the same extent as the addition of the entire PCV genome in the RepR orientation. Unexpectedly, addition of the Pcap sequence in the reverse orientation (PcapR) (SEQ ID NO: 2) also increased grttnc expression level over that of the parent plasmid, pTHgrttnC (FIG. 4). Murine Immunogenicity Comparisons Between pTH and pCV-Based Vectors:

CTL responses in female BALB/c mice elicited by the prototype PCV-based clones, pTHRepgrttnC and pTHRepRgrttnC were compared against those elicited by pTHgrttnC.

IFN-γ ELISPOT assays showed that all three constructs generated CTL responses to 10 out of 15 GrttnC CD4 and CD8 epitopes tested. Because the RT CD8 epitope of GrttnC appears to be immunodominant in Balb/c mice, this epitope was chosen as a marker for comparison of immunogenicity between the PCV-based constructs and pTHgrttnC.

The longevity of the CTL response elicited by 2 intramuscularly (i.m.) administered DNA inoculations of 100 ug each, given 28 days apart, was measured over 90 days following the second DNA inoculation. Five mice per treatment group were tested. CTL responses in the same error range were elicited by pTHgrttnC and pTHRepRgrttnC, while pTHRepgrttnC elicited a superior response (FIG. 5). It was noted that the CTL response levels for pTHgrttnC and pTHRepRgrttnC declined to the same extent over the 90 day test period. By contrast, the CTL response to pTHRepgrttnC was double that of the other constructs at 12 days post priming, dropping to below the level of response seen for the pTH and pTHRepR constructs at 40 days, but then rose so that by 90 days post inoculation, the CTL response for pTHRepgrttnC was again twice that seen for pTHgrttnC and pTHRepRgrttnC. This effect was noticeable for most of the epitopes tested.

The PCV-based vectors were found to be superior to pTH at a 10-fold reduced DNA priming dosage (2× priming doses, 28 days apart, of 10 μg given i.m., 5 female BALB/c mice per treatment). At this level, both pTHRepgrttnC and pTHRepRgrttnC elicited significantly better CTL responses than did pTHgrttnC at either the 10 μg or the 100 μg dose level, with pTHRepgrttnC eliciting the best response (FIG. 6).

The effect of boosting BALB/c mice was tested with a low dose ($10^4$ pfu) of SAAVIMVA-C administered i.m. 56 days after the second of two i.m. DNA inoculations of either 10 μg or 100 μg per dose, given 28 days apart. The boosted response to the RT CD8 epitope in mice primed with 2×10 μg of either pTHRepgrttnC or pTHRepRgrttnC was more than twice that elicited in mice primed with 2×10 μg pTHgrttnC (FIG. 6). In addition, the boosted response after priming at the 10 μg level with pTHRepgrttnC was almost as great as the boosted response after priming with 2×100 μg pTHgrttnC. The boosted response from mice primed with pTHRepRgrttnC was similar at both the 10 μg and the 100 μg levels, and was about 0.75× that elicited after priming with 2×100 μg of either pTHgrttnC or pTHRepRgrttnC (FIG. 6).

In other words, priming with a PCV-based vector at the 10 μg level yielded almost as good a response, after boosting with $10^4$ pfu SAAVIMVA-C, as priming with pTHgrttnC at ten times the priming dose.

It was noted, however, in subsequent experiments, that Prep/rep gene sequences in pTHRep plasmids tended to be unstable, and so all further work was concentrated on the stable pTHRepR construct and its Pcap and PcapR derivatives. The 184 bp Spe I—restricted Pcap—containing sequence (FIG. 8) was sub-cloned into pTHgrttnC so that the fragment was positioned immediately 5' to the CMV immediate/early promoter/enhancer (Pcmv) in pTHgrttnC, to give pTHPcappgrttnC. The 184 bp Spe I restricted Pcap—containing sequence (FIG. 9) was sub-cloned into pTHgrttnC so that the fragment was positioned immediately 5' to the CMV immediate/early promoter/enhancer (Pcmv) in pTHgrttnC, to give pTHPcapRgrttnC.

The Pcap- and PcapR-based vectors were found to be superior to pTH in priming a CTL response to the immunodominant RT epitope of GrttnC in BALB/c mice (2× priming doses, 28 days apart, of 100 μg given i.m., 5 female BALB/c mice per treatment). Both pTHPcapgrttnC and pTHPcapRgrttnC elicited CTL responses in the same error range as pTHRepRgrttnC, but with less variability of response between experiments (FIG. 7).

The mammalian expression vectors described herein show enhanced transgene protein expression levels. This has utility in improving dose efficiency in plasmid-based DNA vaccines, for in vitro mammalian cell expression studies, and potentially for gene therapy use.

In DNA vaccine development, the higher transgene expression level attainable through use of the Pcap-Pcmv and the PcapR-Pcmv promoter combinations allows for a potential 10-fold reduction in vaccine dose necessary to achieve the same cell mediated immune response that can be achieved through the use of a near-identical vaccine construct that uses Pcmv alone (as has been demonstrated so far in a murine immunogenicity model).

While the invention has been described in detail with respect to specific embodiments thereof, it will be appreciated by those skilled in the art that various alterations, modifications and other changes may be made to the claims without departing from the spirit and scope of the present invention. It is therefore intended that this application covers or encompasses all such modifications, alterations and/or changes.

References

Barouch D H, Yang Z Y, Kong W P, et al. (2005). A human T-cell leukemia virus type 1 regulatory element enhances the immunogenicity of human immunodeficiency virus type 1 DNA vaccines in mice and nonhuman primates. J. Virol.; 79: 8828-8834.

Burgers W. A., J. H. van Harmelen, E. Shephard, et al. (2005). Design and preclinical evaluation of a multigene HIV-1 subtype C DNA vaccine for clinical trial. J. Gen Virol, 87:399-410.

Garmory H S, Brown K A, Titball R W (2003). DNA vaccines: improving expression of antigens. Genet Vaccines Ther. 1:2.

Hattermann K, Roedner C, Schmitt C, et al. (2004). Infection studies on human cell lines with porcine circovirus type 1 and porcine circovirus type 2. Xenotransplantation 11:284-294.

Mankertz A, Caliskan R, Hattermann K, et al. (2004). Molecular biology of porcine circovirus; analysis of gene expression and viral replication. Vet Microbiol 98:81-88.

Quintana J, Balasch M, Segales J, et al. (2002). Experimental inoculation of porcine Circoviruses type 1 (PCV1) and type 2 (PCV2) in rabbits and mice. Vet Res 33:220-237.

Velten J, Morey K, Cazzonelli C. (2005). Plant viral intergenic DNA sequence repeats with transcription enhancing activity. Virology Journal 2:16 doi:10.1186/1743-422X-2-16.

http://www.cbrc.jp/research/db/TFSEARCH.html

The invention claimed is:

1. A method for enhancing expression of a transgene from a cytomegalovirus immediate/early promoter (Pcmv) in a host cell comprising the steps of:

(a) inserting a porcine circovirus type 1 capsid gene promoter (Pcap) or a Pcap reverse complement sequence (PcapR) as shown in SEQ ID NOs: 1 or 2 into a mammalian expression cassette upstream (5') of the Pcmv promoter element;

(b) inserting the transgene into the mammalian expression cassette downstream (3') of the Pcmv element;

(c) inserting the expression cassette into the host organism; and (d) causing expression of the transgene.

2. The method of claim 1, wherein a cytomegalovirus intron is inserted downstream (3') of the Pcmv and a bovine growth hormone polyadenylation site (bgh polyA) is inserted downstream (3') of the transgene.

3. The method of claim 1, wherein the Pcap or PcapR is inserted immediately upstream (5') of the Pcmv element.

4. The method of claim 1, wherein the Pcap or PcapR is inserted up to 1100 base pairs upstream (5') of the Pcmv element.

5. The method of claim 1, wherein the host cell is a mammalian cell line for in vitro transgene expression or a cell of a mammalian host organism for in vivo transgene expression.

6. A mammalian expression cassette comprising:

(a) a cytomegalovirus immediate/early promoter (Pcmv) element; and (b) a sequence that is the Pcap or PcapR located upstream (5') of the Pcmv element, wherein the Pcap or PcapR comprises SEQ ID NO: 1 or SEQ ID NO: 2;

wherein the Pcap or PcapR enhances the Pcmv promoter activity.

7. The mammalian expression cassette of claim 6, which includes a transgene downstream (3') of the cytomegalovirus immediate/early promoter element.

8. A vector including the expression cassette of claim 6.

9. An isolated host cell comprising the vector of claim 8.

10. A DNA vaccine comprising the expression cassette or vector as claimed in claims 6 or 8.

* * * * *

SEQUENCE LISTING

```
<160> NUMBER OF SEQ ID NOS: 32

<210> SEQ ID NO 1
<211> LENGTH: 184
<212> TYPE: DNA
<213> ORGANISM: Porcine circovirus 1

<400> SEQUENCE: 1

ctagtaggtg tcgctaggct cagcaaaatt acgggcccac tgactcttcc cacaaccggg     60

cgggcccact atgacgtgta cagctgtctt ccaatcacgc tgctgcatct tcccgctcac    120

tttcaaaagt tcagccagcc cgcggaaatt tctcacatac gttacaggga actgctccat    180

atga                                                                 184


<210> SEQ ID NO 2
<211> LENGTH: 184
<212> TYPE: DNA
<213> ORGANISM: Porcine circovirus 1

<400> SEQUENCE: 2

ctagtcatat ggagcagttc cctgtaacgt atgtgagaaa tttccgcggg ctggctgaac     60

ttttgaaagt gagcgggaag atgcagcagc gtgattggaa gacagctgta cacgtcatag    120

tgggcccgcc cggttgtggg aagagtcagt gggcccgtaa ttttgctgag cctagcgaca    180

ccta                                                                 184


<210> SEQ ID NO 3
<211> LENGTH: 175
<212> TYPE: DNA
<213> ORGANISM: Canary circovirus

<400> SEQUENCE: 3

cgcgcgagag ttcagtgaga tctacgtcaa gtatgggcgt ggtctgaggg atttggccct     60

gatgattgga cagaaacccc gtgacttcaa gacggaagtc gtcgtcatca cagggccttc    120

cggggtgggc aagtcccgac ttgcctctga aatggaagga tcgaagttct acaag         175


<210> SEQ ID NO 4
<211> LENGTH: 175
<212> TYPE: DNA
<213> ORGANISM: Canary circovirus

<400> SEQUENCE: 4

cttgtagaac ttcgatcctt ccatttcaga ggcaagtcgg gacttgccca ccccggaagg     60

ccctgtgatg acgacgactt ccgtcttgaa gtcacggggt ttctgtccaa tcatcagggc    120

caaatccctc agaccacgcc catacttgac gtagatctca ctgaactctc gcgcg         175
```

-continued

<210> SEQ ID NO 5
<211> LENGTH: 180
<212> TYPE: DNA
<213> ORGANISM: Goose circovirus

<400> SEQUENCE: 5
tggcccggaa gtacccgacg acttatgtaa tgtttgggcg gggcttagag cggttgcgtc 60
agctgatcgt ggagaccgct cgtgattgga agacggaggt catcgttctg attgggcggc 120
ctggaagcgg gaagagccgt tacgcgtttg aatttcccgc gcgtgaaaag tattataaat 180

<210> SEQ ID NO 6
<211> LENGTH: 180
<212> TYPE: DNA
<213> ORGANISM: Goose circovirus

<400> SEQUENCE: 6
atttataata cttttcacgc gcgggaaatt caaacgcgta acggctcttc ccgcttccag 60
gccgcccaat cagaacgatg acctccgtct tccaatcacg agcggtctcc acgatcagct 120
gacgcaaccg ctctaagccc cgcccaaaca ttacataagt cgtcgggtac ttccgggcca 180

<210> SEQ ID NO 7
<211> LENGTH: 190
<212> TYPE: DNA
<213> ORGANISM: Duck circovirus

<400> SEQUENCE: 7
tgaggtggcc cggaagttcc ccacgactta tgttatcttt gggcgtggcc tggaacgcct 60
ccgtcacctg atcgttgaga cgcaacgtga ttggaagacc gaagtcatcg ttctgattgg 120
tccgcccggc accgggaaga gccgttatgc atttgaattt cccgccgaaa acaagtatta 180
caaaccacgc 190

<210> SEQ ID NO 8
<211> LENGTH: 190
<212> TYPE: DNA
<213> ORGANISM: Duck circovirus

<400> SEQUENCE: 8
gcgtggtttg taatacttgt tttcggcggg aaattcaaat gcataacggc tcttcccggt 60
gccgggcgga ccaatcagaa cgatgacttc ggtcttccaa tcacgttgcg tctcaacgat 120
caggtgacgg aggcgttcca ggccacgccc aaagataaca taagtcgtgg ggaacttccg 180
ggccacctca 190

<210> SEQ ID NO 9
<211> LENGTH: 180
<212> TYPE: DNA
<213> ORGANISM: Columbid circovirus

<400> SEQUENCE: 9
tcgcgcgaga cttcagtgag atatacgtca agtatgggcg tggcttgcgc gacctgaagc 60
tgctgattgg tcagcagcct cgtgacttca aaacggaagt catcgtcatc acgggcccgc 120
ccggttgcgg gaagagccgt tgggcagctg agtaccccgg aagtaaattt tacaagatga 180

<210> SEQ ID NO 10
<211> LENGTH: 180
<212> TYPE: DNA
<213> ORGANISM: Columbid circovirus

<400> SEQUENCE: 10
tcatcttgta aaatttactt ccggggtact cagctgccca acggctcttc ccgcaaccgg 60
gcgggcccgt gatgacgatg acttccgttt tgaagtcacg aggctgctga ccaatcagca 120
gcttcaggtc gcgcaagcca cgcccatact tgacgtatat ctcactgaag tctcgcgcga 180

<210> SEQ ID NO 11
<211> LENGTH: 180
<212> TYPE: DNA
<213> ORGANISM: Gull circovirus

<400> SEQUENCE: 11
gtgaaatcgc gcgagagttc agtgaagtct acgtcaagta tgggcggggc ctccgtgatc 60
tccggttgct gattggttgc ccgccccgcg atttcaaaac agaagtcatc gttctgattg 120
gcccacctgg ctgtggcaag tcaaaattgg ccaatgagat ggaagggtct aagttctaca 180

<210> SEQ ID NO 12
<211> LENGTH: 180
<212> TYPE: DNA
<213> ORGANISM: Gull circovirus

<400> SEQUENCE: 12
tgtagaactt agacccttcc atctcattgg ccaattttga cttgccacag ccaggtgggc 60
caatcagaac gatgacttct gttttgaaat cgcggggcgg gcaaccaatc agcaaccgga 120
gatcacggag gccccgccca tacttgacgt agacttcact gaactctcgc gcgatttcac 180

<210> SEQ ID NO 13
<211> LENGTH: 180
<212> TYPE: DNA
<213> ORGANISM: Finch circovirus

<400> SEQUENCE: 13
tcgcgcgaga gttcagtcta gcctacgtca gatatgggcg gggcctgcgt gatcttgcgc 60
tgctgattgg ccagaagccc cgtgacttca aaacggaagt catagtgctg accggcccta 120
gtgggtgtgg caaatcccgc tgggccaatg aacaagaagg aactaagttt tataaaatga 180

<210> SEQ ID NO 14
<211> LENGTH: 180
<212> TYPE: DNA
<213> ORGANISM: Finch circovirus

<400> SEQUENCE: 14
tcattttata aaacttagtt ccttcttgtt cattggccca gcgggatttg ccacacccac 60
tagggccggt cagcactatg acttccgttt tgaagtcacg gggcttctgg ccaatcagca 120
gcgcaagatc acgcaggccc cgcccatatc tgacgtaggc tagactgaac tctcgcgcga 180

<210> SEQ ID NO 15
<211> LENGTH: 180
<212> TYPE: DNA
<213> ORGANISM: Beak and feather disease virus AFG3-ZA

<400> SEQUENCE: 15
cgcgcgagag ttcccagata tctacgtcag gcatgggcgg ggcttacata atctctcgct 60
aatggttggt tcccggccac gtgacttcaa gactgaggtc gacgtcatct acggaccacc 120
ggggtgtggc aagagtagat gggccaatga gcagccgggg accaaatatt ataaaatgcg 180

<210> SEQ ID NO 16
<211> LENGTH: 180

-continued

<212> TYPE: DNA
<213> ORGANISM: Beak and feather disease virus AFG3-ZA

<400> SEQUENCE: 16
cgcattttat aatatttggt ccccggctgc tcattggccc atctactctt gccacacccc 60
ggtggtccgt agatgacgtc gacctcagtc ttgaagtcac gtggccggga accaaccatt 120
agcgagagat tatgtaagcc ccgcccatgc ctgacgtaga tatctgggaa ctctcgcgcg 180

<210> SEQ ID NO 17
<211> LENGTH: 190
<212> TYPE: DNA
<213> ORGANISM: Porcine circovirus 2

<400> SEQUENCE: 17
ccgttgcaga gcagcaccct gtaacgtttg tcagaaattt ccgcgggctg gctgaacttt 60
tgaaagtgag cgggaaaatg cagaagcgtg attggaagac taatgtacac gtcattgtgg 120
ggccacctgg gtgtggtaaa agcaaatggg ctgctaattt tgcagacccg gaaaccacat 180
actggaaacc 190

<210> SEQ ID NO 18
<211> LENGTH: 190
<212> TYPE: DNA
<213> ORGANISM: Porcine circovirus 2

<400> SEQUENCE: 18
ggtttccagt atgtggtttc cgggtctgca aaattagcag cccatttgct tttaccacac 60
ccaggtggcc ccacaatgac gtgtacatta gtcttccaat cacgcttctg cattttcccg 120
ctcactttca aaagttcagc cagcccgcgg aaatttctga caaacgttac agggtgctgc 180
tctgcaacgg 190

<210> SEQ ID NO 19
<211> LENGTH: 3687
<212> TYPE: DNA
<213> ORGANISM: Artificial
<220> FEATURE:
<223> OTHER INFORMATION: Sequence of HIV-1 Subtype C gag, reverse transcriptase, tat and nef regions

<400> SEQUENCE: 19
aagcttgcca ccatggctgc tcgcgcatct atcctcagag gcgaaaagtt ggataagtgg 60
gaaaaaatca gactcaggcc aggaggtaaa aaacactaca tgctgaagca tatcgtgtgg 120
gcatctaggg agttggagag atttgcactg aaccccggac tgctggaaac ctcagagggc 180
tgtaagcaaa tcatgaaaca gctccaacca gccttgcaga ccggaacaga agagctgaag 240
tccctttaca ataccgtggc aaccctctat tgcgtccacg agaagatcga ggtgagagac 300
acaaaggagg ccctggacaa aatcgaggag gagcagaata agtgccagca gaagacccag 360
caggcaaagg ctgctgacgg aaaggtctct cagaactatc ctatcgttca gaaccttcag 420
gggcagatgg tgcaccaagc aatcagccct agaaccctga acgcatgggt gaaggtgatc 480
gaggagaaag ccttttctcc cgaggttatc cccatgttta ccgccctgag cgaaggcgcc 540
actcctcaag acctgaacac tatgctgaac acagtgggag gacaccaggc cgctatgcag 600
atgttgaagg ataccatcaa cgaggaggca gccgaatggg accgcctcca ccccgtgcac 660
gccggaccta tcgcccccgg acaaatgaga gaacctcgcg gaagtgatat tgccggtact 720
accagcaccc ttcaagagca gattgcttgg atgaccagca acccacccat cccagtgggc 780

-continued

```
gatatttaca aaaggtggat tattctgggg ctgaacaaaa ttgtgagaat gtactccccc    840

gtctccatcc tcgacatccg ccaaggaccc aaggagcctt ttagggatta cgtggacaga    900

ttcttcaaaa cccttagagc tgagcaagcc actcaggagg ttaagaactg gatgacagat    960

actctgctcg tgcaaaacgc taaccccgat tgcaaaacca tcttgagagc tctcggtcca   1020

ggtgccaccc ttgaggaaat gatgacagca tgtcaaggcg tgggaggacc tgggcacaag   1080

gccagagttc tcgctgaggc catgagccag acaaactcag gcaatatcat gatgcagagg   1140

agtaacttta agggtcccag gagaatcgtc aagtgcttca attgtggcaa ggagggtcac   1200

attgccagga actgccgcgc ccccaggaag aaaggctgct ggaagtgtgg caaagagggc   1260

caccagatga aggattgcac cgagcgccaa gcaaacttcc tgggaaagat ttggcccagt   1320

cataagggcc gccctggcga attctgcggc aagaaggcca tcggcaccgt gctggtgggc   1380

cccacccccg tgaacatcat cggccggaac atgctgaccc agctgggctg caccctgaac   1440

ttccccatca gccccatcga gaccgtgccc gtgaagctga agcccggcat ggacggcccc   1500

aaggtgaagc agtggcccct gaccgaggtg aagatcaagg ccctgaccgc catctgcgag   1560

gagatggaga aggagggcaa gatcaccaag atcggccccg agaaccccta caacaccccc   1620

atcttcgcca tcaagaagga ggacagcacc aagtggcgga agctggtgga cttccgggag   1680

ctgaacaagc ggacccagga cttctgggag gtgcagctgg gcatccccca ccccgccggc   1740

ctgaagaaga agaagagcgt gaccgtgctg gacgtgggcg acgcctactt cagcgtgccc   1800

ctggacgagg gcttccggaa gtacaccgcc ttcaccatcc ccagcatcaa caacgagacc   1860

cccggcatcc ggtaccagta caacgtgctg ccccagggct ggaagggcag ccccgccatc   1920

ttccaggcca gcatgaccaa gatcctggag cccttccggg ccaagaaccc cgagatcgtg   1980

atctaccagt acatggccgc cctgtacgtg ggcagcgacc tggagatcgg ccagcaccgg   2040

gccaagatcg aggagctgcg ggagcacctg ctgaagtggg gcttcaccac ccccgacaag   2100

aagcaccaga aggagccccc cttcctgtgg atgggctacg agctgcaccc cgacaagtgg   2160

accgtgcagc ccatccagct gcccgagaag gacagctgga ccgtgaacga catccagaag   2220

ctggtgggca agctgaactg gaccagccag atctaccccg gcatcaaggt gcggcagctg   2280

tgcaagctgc tgcggggcac caaggccctg accgacatcg tgcccctgac cgaggaggcc   2340

gagctggagc tggccgagaa ccgggagatc ctgaaggagc ccgtgcacgg cgtgtactac   2400

gaccccagca aggacctgat cgccgagatc cagaagcagg gcgacgacca gtggacctac   2460

cagatctacc aggagccctt caagaacctg aaaaccggca agtacgccaa gcggcggacc   2520

acccacacca acgacgtgaa gcagctgacc gaggccgtgc agaagatcag cctggagagc   2580

atcgtgacct ggggcaagac ccccaagttc cggctgccca tccagaagga gacctgggag   2640

atctggtgga ccgactactg gcaggccacc tggatccccg agtgggagtt cgtgaacagc   2700

ggccgcaagc ttgccaccat ggtgggcatc agctacggcc gcaagaagcg ccgccagcgc   2760

cgcagcaccc cgcccagcag cgaggaccac cagaacccca tcagcaagca gcccctgccc   2820

cagacccgcg gcgaccccac cggcagcgag gagagcaaga agaaggtgga gagcaagacc   2880

aagaccgacc ccttcgactg caagtactgc agctaccact gtctggtgtg cttccagacc   2940

aagggcctgg gcatctccta cgggcgcaag aaacggatgg agcccatcga ccccaacctg   3000

gagccctgga accaccccgg cagccagccc aacacccccct gcaacaagtg ctactgcaaa   3060

tactgctcct accactgcct cgtggtgggc tggcccgccg tgcgcgagcg catccgccgc   3120

accgagcccg ccgccgaggg cgtgggcccc gccagccagg acctggacaa gcacggcgcc   3180
```

-continued

```
ctgaccagca gcaacaccgc ccacaacaac cccgactgcg cctggctgca ggcccaggag   3240
gaggaggagg acgtgggctt ccccgtgcgc ccccaggtgc cctgcgcccc catgacctac   3300
aaggccgcct tcgacctgag cttcttcctg aaggagaagg gcggcctgga gggcctgatc   3360
cacagcaagc gccgccagga catcctggac ctgtgggtgt accacaccca gggctacttc   3420
cccgactggc agaactacac ccccggcccc ggcgtgcgct accccctgac cttcggctgg   3480
tgcttcaagc tggtgcccgt ggacccccgc gaggtggagg aggccaacaa gggcgagaac   3540
aactgcctgc tgcaccccat gagccagcac ggcatggagg acgccgaccg cgaggtgctg   3600
cgctgggtgt tcgacagcag cctggcccgc cgccacctgg cccgcgagaa gcaccccgag   3660
tactacaagg actgagaatt ctctaga                                      3687
```

```
<210> SEQ ID NO 20
<211> LENGTH: 4912
<212> TYPE: DNA
<213> ORGANISM: Porcine circovirus

<400> SEQUENCE: 20
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttttgaga    240
tttctgtcgc cgactaaatt catgtcgcgc gatagtggtg tttatcgccg atagagatgg    300
cgatattgga aaaatcgata tttgaaaata tggcatattg aaaatgtcgc cgatgtgagt    360
ttctgtgtaa ctgatatcgc catttttcca aaagtgattt ttgggcatac gcgatatctg    420
gcgatagcgc ttatatcgtt tacgggggat ggcgatagac gactttggtg acttgggcga    480
ttctgtgtgt cgcaaatatc gcagtttcga tataggtgac agacgatatg aggctatatc    540
gccgatagag gcgacatcaa gctggcacat ggccaatgca tatcgatcta tacattgaat    600
caatattggc cattagccat attattcatt ggttatatag cataaatcaa tattggctat    660
tggccattgc atacgttgta tccatatcat aatatgtaca tttatattgg ctcatgtcca    720
acattaccgc catgttgaca ttgattattg actagttatt aatagtaatc aattacgggg    780
tcattagttc atagcccata tatggagttc cgcgttacat aacttacggt aaatggcccg    840
cctggctgac cgcccaacga cccccgccca ttgacgtcaa taatgacgta tgttcccata    900
gtaacgccaa tagggacttt ccattgacgt caatgggtgg agtatttacg gtaaactgcc    960
cacttggcag tacatcaagt gtatcatatg ccaagtacgc cccctattga cgtcaatgac   1020
ggtaaatggc ccgcctggca ttatgcccag tacatgacct tatgggactt tcctacttgg   1080
cagtacatct acgtattagt catcgctatt accatggtga tgcggttttg gcagtacatc   1140
aatgggcgtg gatagcggtt tgactcacgg ggatttccaa gtctccaccc cattgacgtc   1200
aatgggagtt tgttttggca ccaaaatcaa cgggactttc caaaatgtcg taacaactcc   1260
gccccattga cgcaaatggg cggtaggcgt gtacggtggg aggtctatat aagcagagct   1320
cgtttagtga accgtcagat cgcctggaga cgccatccac gctgttttga cctccataga   1380
agacaccggg accgatccag cctccgcggc cgggaacggt gcattggaac gcggattccc   1440
cgtgccaaga gtgacgtaag taccgcctat agagtctata ggcccacccc cttggcttct   1500
tatgcatgct atactgtttt tggcttgggg tctatacacc cccgcttcct catgttatag   1560
gtgatggtat agcttagcct ataggtgtgg gttattgacc attattgacc actcccctat   1620
```

-continued

```
tggtgacgat actttccatt actaatccat aacatggctc tttgccacaa ctctctttat   1680
tggctatatg ccaatacact gtccttcaga gactgacacg gactctgtat ttttacagga   1740
tggggtctca tttattattt acaaattcac atatacaaca ccaccgtccc cagtgcccgc   1800
agtttttatt aaacataacg tgggatctcc acgcgaatct cgggtacgtg ttccggacat   1860
gggctcttct ccggtagcgg cggagcttct acatccgagc cctgctccca tgcctccagc   1920
gactcatggt cgctcggcag ctccttgctc ctaacagtgg aggccagact taggcacagc   1980
acgatgccca ccaccaccag tgtgccgcac aaggccgtgg cggtagggta tgtgtctgaa   2040
aatgagctcg gggagcgggc ttgcaccgct gacgcatttg gaagacttaa ggcagcggca   2100
gaagaagatg caggcagctg agttgttgtg ttctgataag agtcagaggt aactcccgtt   2160
gcggtgctgt taacggtgga gggcagtgta gtctgagcag tactcgttgc tgccgcgcgc   2220
gccaccagac ataatagctg acagactaac agactgttcc tttccatggg tcttttctgc   2280
agtcaccgtc cttgacacga agcttggtac cgagctcgga tccactagta acggccgcca   2340
gtgtgctgga attctgcaga tatccatcac actggcggcc gctcgagcat gcatctagag   2400
ggccctattc tatagtgtca cctaaatgct agagctcgct gatcagcctc gactgtgcct   2460
tctagttgcc agccatctgt tgtttgcccc tcccccgtgc cttccttgac cctggaaggt   2520
gccactccca ctgtcctttc ctaataaaat gaggaaattg catcgcattg tctgagtagg   2580
tgtcattcta ttctgggggg tggggtgggg caggacagca agggggagga ttgggaagac   2640
aatagcaggc atgctgggga tgcggtgggc tctatggctt ctgaggcgga aagaaccagc   2700
tggggctcga gggggggatcg atcccgtcga cctcgagagc ttggcgtaat catggtcata   2760
gctgtttcct gtgtgaaatt gttatccgct cacaattcca cacaacatac gagccggaag   2820
cataaagtgt aaagcctggg gtgcctaatg agtgagctaa ctcacattaa ttgcgttgcg   2880
ctcactgccc gctttccagt cgggaaacct gtcgtgccag ctgcattaat gaatcggcca   2940
acgcgcgggg agaggcggtt tgcgtattgg gcgctcttcc gcttcctcgc tcactgactc   3000
gctgcgctcg gtcgttcggc tgcggcgagc ggtatcagct cactcaaagg cggtaatacg   3060
gttatccaca gaatcagggg ataacgcagg aaagaacatg tgagcaaaag gccagcaaaa   3120
ggccaggaac cgtaaaaagg ccgcgttgct ggcgtttttc cataggctcc gcccccctga   3180
cgagcatcac aaaaatcgac gctcaagtca gaggtggcga aacccgacag gactataaag   3240
ataccaggcg tttccccctg gaagctccct cgtgcgctct cctgttccga ccctgccgct   3300
taccggatac ctgtccgcct ttctcccttc gggaagcgtg gcgctttctc aatgctcacg   3360
ctgtaggtat ctcagttcgg tgtaggtcgt tcgctccaag ctgggctgtg tgcacgaacc   3420
ccccgttcag cccgaccgct gcgccttatc cggtaactat cgtcttgagt ccaacccggt   3480
aagacacgac ttatcgccac tggcagcagc cactggtaac aggattagca gagcgaggta   3540
tgtaggcggt gctacagagt tcttgaagtg gtggcctaac tacggctaca ctagaaggac   3600
agtatttggt atctgcgctc tgctgaagcc agttaccttc ggaaaaagag ttggtagctc   3660
ttgatccggc aaacaaacca ccgctggtag cggtggtttt tttgtttgca agcagcagat   3720
tacgcgcaga aaaaaaggat ctcaagaaga tcctttgatc ttttctacgg ggtctgacgc   3780
tcagtggaac gaaaactcac gttaagggat tttggtcatg agattatcaa aaaggatctt   3840
cacctagatc cttttaaatt aaaaatgaag ttttaaatca atctaaagta tatatgagta   3900
aacttggtct gacagttacc aatgcttaat cagtgaggca cctatctcag cgatctgtct   3960
atttcgttca tccatagttg cctgactccc cgtcgtgtag ataactacga tacgggaggg   4020
```

-continued

```
cttaccatct ggccccagtg ctgcaatgat accgcgagac ccacgctcac cggctccaga   4080

tttatcagca ataaaccagc cagccggaag ggccgagcgc agaagtggtc ctgcaacttt   4140

atccgcctcc atccagtcta ttaattgttg ccgggaagct agagtaagta gttcgccagt   4200

taatagtttg cgcaacgttg ttgccattgc tacaggcatc gtggtgtcac gctcgtcgtt   4260

tggtatggct tcattcagct ccggttccca acgatcaagg cgagttacat gatcccccat   4320

gttgtgcaaa aaagcggtta gctccttcgg tcctccgatc gttgtcagaa gtaagttggc   4380

cgcagtgtta tcactcatgg ttatggcagc actgcataat tctcttactg tcatgccatc   4440

cgtaagatgc ttttctgtga ctggtgagta ctcaaccaag tcattctgag aatagtgtat   4500

gcggcgaccg agttgctctt gcccggcgtc aatacgggat aataccgcgc cacatagcag   4560

aactttaaaa gtgctcatca ttggaaaacg ttcttcgggg cgaaaactct caaggatctt   4620

accgctgttg agatccagtt cgatgtaacc cactcgtgca cccaactgat cttcagcatc   4680

ttttactttc accagcgttt ctgggtgagc aaaaacagga aggcaaaatg ccgcaaaaaa   4740

gggaataagg gcgacacgga aatgttgaat actcatactc ttcctttttc aatattattg   4800

aagcatttat cagggttatt gtctcatgag cggatacata tttgaatgta tttagaaaaa   4860

taaacaaata ggggttccgc gcacatttcc ccgaaaagtg ccacctgacg tc           4912


<210> SEQ ID NO 21
<211> LENGTH: 1777
<212> TYPE: DNA
<213> ORGANISM: Porcine circovirus

<400> SEQUENCE: 21

ctagtctcga cattggtgtg ggtatttaaa tggagccaca gctggtttct tttattattt     60

ggctggaacc aatcaattgt ttggtccagc tcaggtttgg gggtgaagta cctggagtgg    120

taggtaaagg gctgccttat ggtgtggcgg gaggagtagt taatataggg gtcataggcc    180

aagttggtgg agggggttac aaagttggca tccaagataa cagcagtgga cccaacacct    240

ctttgattag aggtgatggg gtctctgggg taaaattcat atttagcctt tctaatacgg    300

tagtattgga aaggtagggg taggggggttg gtgccgcctg aggggggggag gaactggccg    360

atgttgaatc tgagctggtt aacattccaa gatggctgcg agtgtcctcc ttctatggtg    420

agtacaaatt ctctagaaag gcggcaattg aagataccg tctttcggcg ccatctgtaa    480

cggtttctga aggcggggtg tgccaaatat ggtcttctgc ggaggatgtt tccaagatgg    540

ctgcgggggc gggtccttct tctgcggtaa cgcctccttg gccacgtcat cctataaaag    600

tgaaagaagt gcgctgctgt agtattacca gcgcacttcg gcagcggcag cacctcggca    660

gcgtcggtga aaatgccaag caagaaaagc ggcccgcaac ccataagag gtgggtgttc    720

acccttaata atccttccga ggaggagaaa aacaaaatac gggagcttcc aatctccctt    780

tttgattatt ttgtttgcgg agaggaaggt ttggaagagg gtagaactcc tcacctccag    840

ggtttgcga attttgctaa gaagcagact tttaacaagg tgaagtggta ttttggtgcc    900

cgctgccaca tcgagaaagc gaaaggaacc gaccagcaga ataaagaata ctgcagctgc    960

agtaaagaag gccacatact tatcgagtgt ggagctccgc ggaaccaggg gaagcgcagc   1020

gacctgtcta ctgctgtgag taccctttg gagacggggt ctttggtgac tgtagccgag   1080

cagttccctg taacgtatgt gagaaatttc cgcgggctgg ctgaactttt gaaagtgagc   1140

gggaagatgc agcagcgtga ttggaagaca gctgtacacg tcatagtggg cccgcccggt   1200

tgtgggaaga gccagtgggc ccgtaatttt gctgagccta gcgacaccta ctggaagcct   1260
```

-continued

```
agtagaaata agtggtggga tggatatcat ggagaagaag ttgttgtttt ggatgatttt   1320

tatggctggt taccttggga tgatctactg agactgtgtg accggtatcc attgactgta   1380

gagactaaag gggtactgt tcctttttttg gcccgcagta ttttgattac cagcaatcag   1440

gcccccccagg aatggtactc ctcaactgct gtcccagctg tagaagctct ctatcggagg   1500

attactactt tgcaattttg gaagactgct ggagaacaat ccacggaggt acccgaaggc   1560

cgatttgaag cagtggaccc accctgtgcc cttttcccat ataaaataaa ttactgagtc   1620

ttttttgtta tcacatcgta atggttttta tttttattca tttagagggt cttttaggat   1680

aaattctctg aattgtacat aaatagtcag ccttaccaca taattttggg ctgtggctgc   1740

attttggagc gcatagccga ggcctgtgtg acaatca                             1777
```

<210> SEQ ID NO 22
<211> LENGTH: 1777
<212> TYPE: DNA
<213> ORGANISM: Porcine circovirus

<400> SEQUENCE: 22

```
ctagtgattg tcacacaggc ctcggctatg cgctccaaaa tgcagccaca gcccaaaatt     60

atgtggtaag gctgactatt tatgtacaat tcagagaatt tatcctaaaa gaccctctaa    120

atgaataaaa ataaaaacca ttacgatgtg ataacaaaaa agactcagta atttatttta    180

tatgggaaaa gggcacaggg tgggtccact gcttcaaatc ggccttcggg tacctccgtg    240

gattgttctc cagcagtctt ccaaaattgc aaagtagtaa tcctccgata gagagcttct    300

acagctggga cagcagttga ggagtaccat tcctgggggg cctgattgct ggtaatcaaa    360

atactgcggg ccaaaaaagg aacagtaccc cctttagtct ctacagtcaa tggataccgg    420

tcacacagtc tcagtagatc atcccaaggt aaccagccat aaaaatcatc caaaacaaca    480

acttcttctc catgatatcc atcccaccac ttatttctac taggcttcca gtaggtgtcg    540

ctaggctcag caaaattacg ggcccactgg ctcttcccac aaccgggcgg gcccactatg    600

acgtgtacag ctgtcttcca atcacgctgc tgcatcttcc cgctcacttt caaaagttca    660

gccagcccgc ggaaatttct cacatacgtt acagggaact gctcggctac agtcaccaaa    720

gaccccgtct ccaaaagggt actcacagca gtagacaggt cgctgcgctt cccctggttc    780

cgcggagctc cacactcgat aagtatgtgg ccttctttac tgcagctgca gtattcttta    840

ttctgctggt cggttccttt cgctttctcg atgtggcagc gggcaccaaa ataccacttc    900

accttgttaa aagtctgctt cttagcaaaa ttcgcaaacc cctggaggtg aggagttcta    960

ccctcttcca aaccttcctc tccgcaaaca aaataatcaa aaagggagat tggaagctcc   1020

cgtattttgt ttttctcctc ctcggaagga ttattaaggg tgaacaccca cctcttatgg   1080

ggttgcgggc cgcttttctt gcttggcatt ttcaccgacg ctgccgaggt gctgccgctg   1140

ccgaagtgcg ctggtaatac tacagcagcg cacttctttc acttttatag gatgacgtgg   1200

ccaaggaggc gttaccgcag aagaaggacc cgcccccgca gccatcttgg aaacatcctc   1260

cgcagaagac catatttggc acaccccgcc ttcagaaacc gttacagatg gcgccgaaag   1320

acgggtatct tcaattgccg cctttctaga gaatttgtac tcaccataga aggaggacac   1380

tcgcagccat cttggaatgt taaccagctc agattcaaca tcggccagtt cctccccccc   1440

tcaggcggca ccaacccccct acccctacct ttccaatact accgtattag aaaggctaaa   1500

tatgaatttt accccagaga ccccatcacc tctaatcaaa gaggtgttgg gtccactgct   1560

gttatcttgg atgccaactt tgtaaccccc tccaccaact tggcctatga cccctatatt   1620
```

aactactcct cccgccacac cataaggcag ccctttacct accactccag gtacttcacc 1680
cccaaacctg agctggacca aacaattgat tggttccagc caaataataa aagaaaccag 1740
ctgtggctcc atttaaatac ccacaccaat gtcgaga 1777

<210> SEQ ID NO 23
<211> LENGTH: 752
<212> TYPE: DNA
<213> ORGANISM: Porcine circovirus

<400> SEQUENCE: 23
attctctaga aaggcggcaa ttgaagatac ccgtctttcg gcgccatctg taacggtttc 60
tgaaggcggg gtgtgccaaa tatggtcttc tccggaggat gtttccaaga tggctgcggg 120
ggcgggtcct tcttctgcgg taacgcctcc ttggccacgt catcctataa aagtgaaaga 180
agtgcgctgc tgtagtatta ccagcgcact tcggcagcgg cagcacctcg gcagcgtcag 240
tgaaaatgcc aagcaagaaa agcggcccgc aaccccataa gaggtgggtg ttcaccctta 300
ataatccttc cgaggaggag aaaaacaaaa tacgggagct tccaatctcc ctttttgatt 360
attttgtttg cggagaggaa ggtttggaag agggtagaac tcctcacctc caggggtttg 420
cgaattttgc taagaagcag acttttaaca aggtgaagtg gtattttggt gcccgctgcc 480
acatcgagaa agcgaaagga accgaccagc agaataaaga atactgcagt aaagaaggcc 540
acatacttat cgagtgtgga gctccgcgga accaggggaa gcgcagcgac ctgtctactg 600
cttattttga ttaccagcaa tcaggccccc caggaatggt actcctcaac tgctgtccca 660
gctgtagaag ctctctatcg gaggattact actttgcaat tttggaagac tgctggagaa 720
caatccacgg aggtacccga aggccgattt ga 752

<210> SEQ ID NO 24
<211> LENGTH: 350
<212> TYPE: DNA
<213> ORGANISM: Porcine circovirus

<400> SEQUENCE: 24
attctctaga aaggcggcaa ttgaagatac ccgtctttcg gcgccatctg taacggtttc 60
tgaaggcggg gtgtgccaaa tatggtcttc tccggaggat gtttccaaga tggctgcggg 120
ggcgggtcct tcttctgcgg taacgcctcc ttggccacgt catcctataa aagtgaaaga 180
agtgcgctgc tgtagtatta ccagcgcact tcggcagatc aggcccccca ggaatggtac 240
tcctcaactg ctgtcccagc tgtagaagct ctctatcgga ggattactac tttgcaattt 300
tggaagactg ctggagaaca atccacggag gtacccgaag gccgatttga 350

<210> SEQ ID NO 25
<211> LENGTH: 17
<212> TYPE: DNA
<213> ORGANISM: Artificial
<220> FEATURE:
<223> OTHER INFORMATION: Primer sequence

<400> SEQUENCE: 25
cctaactacg gctacac 17

<210> SEQ ID NO 26
<211> LENGTH: 18
<212> TYPE: DNA
<213> ORGANISM: Artificial
<220> FEATURE:
<223> OTHER INFORMATION: Primer sequence -continued

<400> SEQUENCE: 26
cgtagttatc tacacgac 18

<210> SEQ ID NO 27
<211> LENGTH: 190
<212> TYPE: DNA
<213> ORGANISM: Porcine circovirus

<400> SEQUENCE: 27
actagtaggt gtcgctaggc tcagcaaaat tacgggccca ctgactcttc ccacaaccgg 60
gcgggcccac tatgacgtgt acagctgtct tccaatcacg ctgctgcatc ttcccgctca 120
ctttcaaaag ttcagccagc ccgcggaaat ttctcacata cgttacaggg aactgctcca 180
tatgactagt 190

<210> SEQ ID NO 28
<211> LENGTH: 190
<212> TYPE: DNA
<213> ORGANISM: Porcine circovirus

<400> SEQUENCE: 28
actagtcata tggagcagtt ccctgtaacg tatgtgagaa atttccgcgg gctggctgaa 60
cttttgaaag tgagcgggaa gatgcagcag cgtgattgga agacagctgt acacgtcata 120
gtgggcccgc ccggttgtgg gaagagtcag tgggcccgta attttgctga gcctagcgac 180
acctactagt 190

<210> SEQ ID NO 29
<211> LENGTH: 1783
<212> TYPE: DNA
<213> ORGANISM: Porcine circovirus

<400> SEQUENCE: 29
actagtctcg acattggtgt gggtatttaa atggagccac agctggtttc ttttattatt 60
tggctggaac caatcaattg tttggtccag ctcaggtttg ggggtgaagt acctggagtg 120
gtaggtaaag ggctgcctta tggtgtggcg ggaggagtag ttaatatagg ggtcataggc 180
caagttggtg gagggggtta caaagttggc atccaagata acagcagtgg acccaacacc 240
tctttgatta gaggtgatgg ggtctctggg gtaaaattca tatttagcct ttctaatacg 300
gtagtattgg aaaggtaggg gtagggggtt ggtgccgcct gagggggggga ggaactggcc 360 gatgttgaat ctgagctggt taacattcca agatggctgc gagtgtcctc cttctatggt 420
gagtacaaat tctctagaaa ggcggcaatt gaagataccc gtctttcggc gccatctgta 480
acggtttctg aaggcggggt gtgccaaata tggtcttctg cggaggatgt ttccaagatg 540
gctgcggggg cgggtccttc ttctgcggta acgcctcctt ggccacgtca tcctataaaa 600
gtgaaagaag tgcgctgctg tagtattacc agcgcacttc ggcagcggca gcacctcggc 660
agcgtcggtg aaaatgccaa gcaagaaaag cggcccgcaa ccccataaga ggtgggtgtt 720
cacccttaat aatccttccg aggaggagaa aaacaaaata cgggagcttc caatctccct 780
ttttgattat tttgtttgcg gagaggaagg tttggaagag ggtagaactc ctcacctcca 840
ggggtttgcg aattttgcta agaagcagac ttttaacaag gtgaagtggt attttggtgc 900
ccgctgccac atcgagaaag cgaaaggaac cgaccagcag aataaagaat actgcagctg 960
cagtaaagaa ggccacatac ttatcgagtg tggagctccg cggaaccagg ggaagcgcag 1020
cgacctgtct actgctgtga gtaccctttt ggagacgggg tctttggtga ctgtagccga 1080

-continued

```
gcagttccct gtaacgtatg tgagaaattt ccgcgggctg gctgaacttt tgaaagtgag   1140

cgggaagatg cagcagcgtg attggaagac agctgtacac gtcatagtgg gcccgcccgg   1200

ttgtgggaag agccagtggg cccgtaattt tgctgagcct agcgacacct actggaagcc   1260

tagtagaaat aagtggtggg atggatatca tggagaagaa gttgttgttt tggatgattt   1320

ttatggctgg ttaccttggg atgatctact gagactgtgt gaccggtatc cattgactgt   1380

agagactaaa gggggtactg ttcctttttt ggcccgcagt attttgatta ccagcaatca   1440

ggccccccag gaatggtact cctcaactgc tgtcccagct gtagaagctc tctatcggag   1500

gattactact ttgcaatttt ggaagactgc tggagaacaa tccacggagg tacccgaagg   1560

ccgatttgaa gcagtggacc caccctgtgc ccttttccca tataaaataa attactgagt   1620

ctttttttgtt atcacatcgt aatggttttt atttttattc atttagaggg tcttttagga   1680

taaattctct gaattgtaca taaatagtca gccttaccac ataattttgg gctgtggctg   1740

cattttggag cgcatagccg aggcctgtgt gacaatcact agt                     1783
```

<210> SEQ ID NO 30
<211> LENGTH: 1783
<212> TYPE: DNA
<213> ORGANISM: Porcine circovirus

<400> SEQUENCE: 30

```
actagtgatt gtcacacagg cctcggctat gcgctccaaa atgcagccac agcccaaaat     60

tatgtggtaa ggctgactat ttatgtacaa ttcagagaat ttatcctaaa agaccctcta    120

aatgaataaa aataaaaacc attacgatgt gataacaaaa aagactcagt aatttatttt    180

atatgggaaa agggcacagg gtgggtccac tgcttcaaat cggccttcgg gtacctccgt    240

ggattgttct ccagcagtct tccaaaattg caaagtagta atcctccgat agagagcttc    300

tacagctggg acagcagttg aggagtacca ttcctggggg gcctgattgc tggtaatcaa    360

aatactgcgg gccaaaaaag gaacagtacc ccctttagtc tctacagtca atggataccg    420

gtcacacagt ctcagtagat catcccaagg taaccagcca taaaaatcat ccaaaacaac    480

aacttcttct ccatgatatc catcccacca cttatttcta ctaggcttcc agtaggtgtc    540

gctaggctca gcaaaattac gggcccactg gctcttccca caaccgggcg ggcccactat    600

gacgtgtaca gctgtcttcc aatcacgctg ctgcatcttc ccgctcactt tcaaaagttc    660

agccagcccg cggaaatttc tcacatacgt tacagggaac tgctcggcta cagtcaccaa    720

agaccccgtc tccaaaaggg tactcacagc agtagacagg tcgctgcgct tcccctggtt    780

ccgcggagct ccacactcga taagtatgtg gccttcttta ctgcagctgc agtattcttt    840

attctgctgg tcggttcctt tcgctttctc gatgtggcag cgggcaccaa aataccactt    900

caccttgtta aaagtctgct tcttagcaaa attcgcaaac ccctggaggt gaggagttct    960

accctcttcc aaaccttcct ctccgcaaac aaaataatca aaaagggaga ttggaagctc   1020

ccgtattttg tttttctcct cctcggaagg attattaagg gtgaacaccc acctcttatg   1080

gggttgcggg ccgcttttct tgcttggcat tttcaccgac gctgccgagg tgctgccgct   1140

gccgaagtgc gctggtaata ctacagcagc gcacttcttt cacttttata ggatgacgtg   1200

gccaaggagg cgttaccgca gaagaaggac ccgcccccgc agccatcttg gaaacatcct   1260

ccgcagaaga ccatatttgg cacaccccgc cttcagaaac cgttacagat ggcgccgaaa   1320

gacgggtatc ttcaattgcc gcctttctag agaatttgta ctcaccatag aaggaggaca   1380

ctcgcagcca tcttggaatg ttaaccagct cagattcaac atcggccagt tcctcccccc   1440
```

-continued

```
ctcaggcggc accaaccccc tacccctacc tttccaatac taccgtatta gaaaggctaa   1500

atatgaattt taccccagag accccatcac ctctaatcaa agaggtgttg ggtccactgc   1560

tgttatcttg gatgccaact ttgtaacccc ctccaccaac ttggcctatg acccctatat   1620

taactactcc tcccgccaca ccataaggca gccctttacc taccactcca ggtacttcac   1680

ccccaaacct gagctggacc aaacaattga ttggttccag ccaaataata aaagaaacca   1740

gctgtggctc catttaaata cccacaccaa tgtcgagact agt                     1783


<210> SEQ ID NO 31
<211> LENGTH: 201
<212> TYPE: DNA
<213> ORGANISM: Finch circovirus

<400> SEQUENCE: 31

ccgtgaaagc cggaagaggt atggccgaag tcgcgcgaga gttcagtcta gcctacgtca     60

gatatgggcg gggcctgcgt gatcttgcgc tgctgattgg ccagaagccc cgtgacttca    120

aaacggaagt catagtgctg accggcccta gtgggtgtgg caaatcccgc tgggccaatg    180

aacaagaagg aactaagttt t                                             201


<210> SEQ ID NO 32
<211> LENGTH: 200
<212> TYPE: DNA
<213> ORGANISM: Goose circovirus

<400> SEQUENCE: 32

tggtctgccg ataactgacg tggcccggaa gtacccgacg acttatgtaa tgtttgggcg     60

gggcttagag cggttgcgtc agctgatcgt ggagaccgct cgtgattgga agacggaggt    120

catcgttctg attgggcggc ctggaagcgg gaagagccgt tacgcgtttg aatttcccgc    180

gcgtgaaaag tattataaat                                               200
```